United States Patent
Sandanayaka et al.

(10) Patent No.: US 6,489,316 B2
(45) Date of Patent: Dec. 3, 2002

(54) 6-(SPIROCYCLOPROPYL) PENICILLANIC ACID 4, 4-DIOXIDES

(75) Inventors: Vincent P. Sandanayaka, Westley Hills; Amarnauth S. Prashad, Garnerville, both of NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/771,440

(22) Filed: Jan. 26, 2001

(65) Prior Publication Data

US 2002/0147178 A1 Oct. 10, 2002

Related U.S. Application Data

(60) Provisional application No. 60/266,310, filed on Jan. 26, 2000, now abandoned.

(51) Int. Cl.[7] .................... C07D 499/10; C07D 499/90; A61K 31/04; A61P 31/428
(52) U.S. Cl. ................. 514/193; 540/307; 540/312
(58) Field of Search ................. 514/193; 540/307, 540/312

(56) References Cited

U.S. PATENT DOCUMENTS 4,695,628 A 9/1987 Bos et al. ................ 540/312

OTHER PUBLICATIONS

Arrowsmith, J. E.; Greengrass, C. W.; Newman, M. J., Tetrahedron, 39(15), 2469–75 (English) 1983.*
Campbell, Malcolm M.; Harcus, Robert G.; Ray, Stephen J., Tetrahedron Lett. (16), 1441–4 (English) 1979.*
S.A. Matlin, L. Chan, B. Catherwood, J. Chem. Soc., Perkin Trans I, 1990, 89–96.
K. Bush, G.A. Jacoby, and A.A. Medeiros in "Antimicrobial Agents and Chemotherapy", vol. 39, 1995, pp. 1211–1233.
Org. Synthesis, Coll. vol. 3, 35.
Campbell, M.M., Harcus, R.G., Tetrahedron Letters, No. 16, 1979, 1441.
Arrowsmith, J.E., Greengrass, C.W., Newman, M.J., Tetrahedron, 39, 1983, 2469.
H.C. Neu, "Antibiotic Inhibitors of Bacterial Cell Wall Biosynthesis" D.T. Tipper ed. Pergaman Press 1987, pp. 241–259.
N.A. Kuck; N.V. Jacobs; P.J. Peterson; W.J. Weiss; and R.T. Testa, in "Antimicrobial Agents and Chemotherapy", vol. 33, 1989, pp. 1964–1969.

* cited by examiner

Primary Examiner—Mukund J. Shah
Assistant Examiner—Thomas McKenzie
(74) Attorney, Agent, or Firm—Daniel B. Moran

(57) ABSTRACT

The 6-(spirocyclopropyl)-penicillanic acid 4,4-dioxides of the general Formula (I):

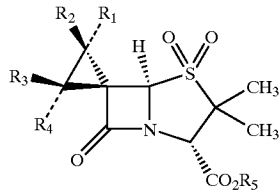

Formula (I)

as defined herein above which exhibit beta-lactamase inhibiting activity, use of such compounds in combination with beta-lactam antibiotics for inhibiting beta-lactamases, pharmaceutical compositions and processes for preparing such compounds.

38 Claims, No Drawings

6-(SPIROCYCLOPROPYL) PENICILLANIC ACID 4, 4-DIOXIDES

This application claims benefit of U.S. Provisional Application No. 60/266,310 which was converted from U.S. patent application Ser. No. 09/491,775 filed Jan. 26, 2000, now abandoned, pursuant to a petition filed under 37 C.F.R. 1.53 (c) (2) filed Apr. 20, 2000.

BACKGROUND OF THE INVENTION

1. Field of the Invention

The invention relates to 6-(spirocyclopropyl)-penicillanic acid 4,4-dioxides and non-toxic pharmaceutically acceptable salts thereof, useful as beta-lactamase inhibitors. The present 6-(spirocyclopropyl)-penicillanic acid 4,4-dioxides and pharmaceutical compositions thereof are useful as beta-lactamase inhibitors and as beta-lactamase inhibitors in combination with other beta-lactam antibiotics for use in humans and animals. The present invention also provides certain novel intermediates and processes for the preparation of the penicillanic acid 4,4-dioxide beta-lactamase inhibitors.

2. Description of the Prior Art

A well-known and widely used class of antibacterial compounds are the beta-lactam antibiotics. These antibiotics are characterized by the common structural unit, 2-azetidinone (beta-lactam) moiety. When this moiety is fused to a thiazolidone ring, the corresponding compounds are referred to generically as penicillins and when the fused ring is a dihydrothiazine ring, the compounds are referred to as cephalosporins. Typical examples of penicillins include penicillin G, penicillin V, ampicillin and amoxicillin and typical examples of cephalosporins include cefazolin, cephalexin, and cephalothin, all of which are commonly used clinically.

Despite the wide use of the beta-lactam antibiotics as valuable chemotherapeutic agents against pathogenic microorganisms, emerging resistance against beta-lactam antibiotics has limited their application. Pathogenic microorganisms produce beta-lactamase enzymes, which in turn inactivate conventional beta-lactam antibiotics which include penicillins and cephalosporins. Beta-lactamases are enzymes which cleave the beta-lactam ring of penicillins and cephalosporins, causing the antibiotic to lose its antibacterial activity. The use of a beta-lactamase inhibitor in combination with a beta-lactam drug potentiates the effectiveness of the requisite antibiotic against the resistant or partially resistant microorganisms. The principle of potentiation by beta-lactamase inhibitors is discussed by H. C. Neu, "Antibiotic Inhibitors of Bacterial Cell Wall Biosynthesis", D. T. Tipper ed. Pergaman Press, 1987, pp. 241–259.

The various beta-lactamase enzymes may be categorized according to structural similarities, or biochemical function with respect to their ability to hydrolyze certain beta-lactam antibiotics. Beta-lactamase enzymes of group 1 (class C), group 2 (class A) and group 4 hydrolyze predominantly cephalosporins and/or penicillins by utilizing the amino acid serine at their active site. Beta-lactamases of group 3 (class B) known as metallo-beta-lactamases utilize a metal ion (commonly zinc) as the beta-lactam hydrolyzing functionality. Metallo-beta-lactamases can hydrolyze penicillin, cephalosporin and carbapenem classes of antibiotics. The currently marketed beta-lactamase inhibitors(clavulanic acid, sulbactam, and tazobactam) are clinically effective against class A beta-lactam enzymes. A detailed explanation of the classification of beta-lactamase enzymes is described in K. Bush, G. A. Jacoby, and A. A. Medeiros in "Antimicrobial Agents and Chemotherapy", Vol. 39, 1995, pages 1211–1233.

Certain spirocyclopropyl penicillanic acid derivatives are disclosed: Sheehan, J. C., Chacko, E., Lo, Y. S., Ponzi, D. R., Sato, E., *J.Org. Chem.*, 43, No 25, 1978, 4856; Campbell, M. M., Harcus, R. G., *Tetrahedron Letters*, No 16, 1979, 1441; and Arrowsmith, J. E., Greengrass, C. W., Newman, M. J., *Tetrahedron,* 39, 1983, 2469.

The novel 6-(spirocyclopropyl)penicillanic acid 4,4-dioxides of the present invention exhibit broad spectrum inhibitory activity against beta-lactamases of different classes, and in particular inhibitory activity against group 1 (class C) and group 2 (class A).

SUMMARY OF THE INVENTION

The invention relates to novel compounds selected from those of the general Formula (I):

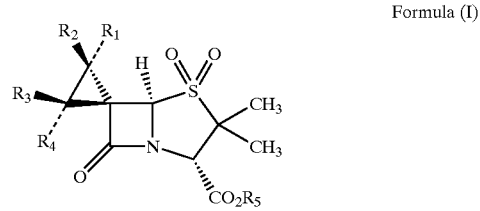

Formula (I)

wherein:
$R_1$, $R_2$, $R_3$, and $R_4$ are independently selected from H, —OH and —OR$_6$;

$R_5$ is selected from hydrogen, an alkali metal cation, an alkaline earth metal cation, ammonium, tetraalkylammonium, alkyl of 1 to 12 carbon atoms, cycloalkyl of 3 to 10 carbon atoms, alkenyl of 2 to 12 carbon atoms, aralkyl of 7 to 20 carbon atoms, aryl of 6 to 12 carbon atoms and moieties of the formulae:

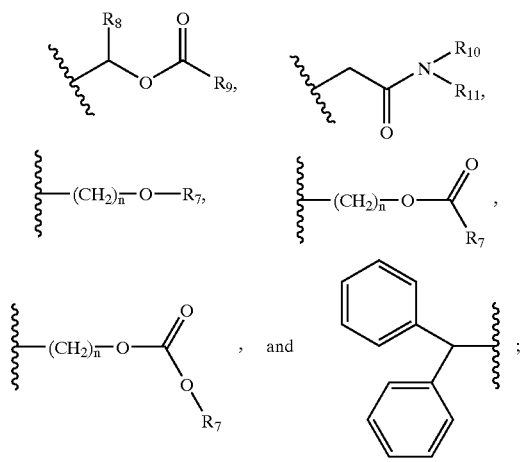

$R_6$ is selected from alkyl of 1 to 12 carbon atoms optionally substituted with alkoxy, halogen, dialkylamino, -Oalkyloalkyl, and 1 or 2 phenyl groups; cycloalkyl of 3 to 10 carbon atoms; alkenyl of 2 to 12 carbon atoms; alkyloxacyclopropyl of 3 to 12 carbon atoms; aryl of 6 to 12 carbon atoms; heteroaryl having 5 or 6 ring atoms; bicyclic heteroaryl having 8 to 20 ring atoms; heteroarylalkyl having 5 or 6 ring atoms; and —SiR$_{12}$R$_{13}$R$_{14}$;

n is an integer of 1 to 3;

$R_7$ is selected from alkyl of 1 to 12 carbon atoms; cycloalkyl of 3 to 10 carbon atoms; aralkyl of 7 to 20 carbon atoms; and aryl of 6 to 12 carbon atoms;

$R_8$, $R_9$, $R_{10}$ and $R_{11}$ are independently selected from alkyl of 1 to 12 carbon atoms;

$R_{12}$ $R_{13}$ and $R_{14}$ are independently selected from alkyl of 1 to 12 carbon atoms optionally substituted with —$OCOR_7$, —$CO_2R_7$, alkenyl of 2 to 12 carbon atoms, cycloalkyl of 3 to 10 carbon atoms; and aryl of 6 to 12 carbon atoms; optionally two of $R_{12}$, $R_{13}$, and $R_{14}$ taken together with the silicon atom to which they are attached form a cyclic ring of 5 or 6 ring atoms;

provided that at least one of $R_1$, $R_2$, $R_3$, and $R_4$ is hydrogen; or a pharmaceutically acceptable salt thereof.

Among the preferred compounds of Formula (I) of this invention are those in the subgroups, and pharmaceutically acceptable salts thereof:

a) $R_5$ is selected from H, sodium, lithium and potassium;

b) $R_5$ is selected from aralkyl of 7 to 20 carbon atoms,

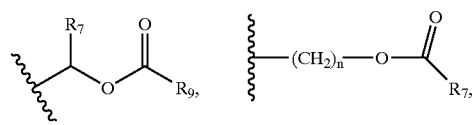

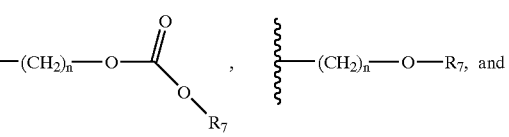

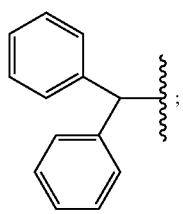

c) $R_5$ is selected from H, Na, Li, K,

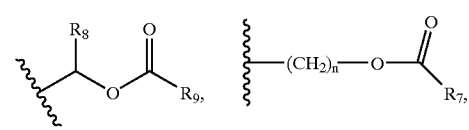

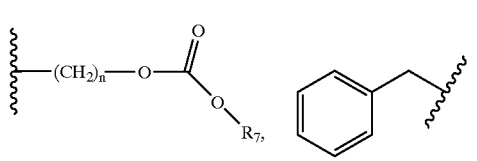

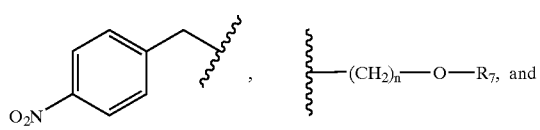

$R_1$ is selected from —$OCH_3$, —$OCH_2CH_2OCH_3$, —$OCH_2CH_2Cl$, —$OCH_2CH_2N(CH_3)_2$, —O—cyclohexyl, —$OC(CH_3)_2CH_2CH_3$, —$OCH=CHCH_3$, —$OCH_2$(tetrahydrofuran), —$OCH_2CH_2OCH_2CH_2OCH_2CH_3$, —$OSi(CH_3)_2$t-butyl, —$OSi(CH_3)_2$phenyl, —$OSi(CH_3)_2CH_2CH=CH_2$, —$OSi(CH_3)_2CH_2CH_3$, —$OSi(CH_3)_2$-propyl, $OSi(CH_3)_2CH=CH_2$, —$OSi(CH_3)_2CH_2CH_2OCOCH_3$, —$OSi(phenyl)_3$, —$OCH_2CH=CH_2$, —O-t-butyl, —$OCH(phenyl)_2$ —$OSiMe_2$(cyclohexyl)

and 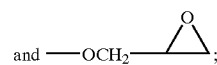;

d) $R_6$ is selected from alkyl of 1 to 12 carbon atoms optionally substituted with alkoxy, halogen, dialkylamino, -Oalkyloalkyl, and 1 or 2 phenyl groups; cycloalkyl of 3 to 10 carbon atoms; alkenyl of 2 to 12 carbon atoms; alkyloxacyclopropyl of 3 to 12 carbon atoms; aryl of 6 to 12 carbon atoms; heteroaryl having 5 or 6 ring atoms; bicyclic heteroaryl having 8 to 20 ring atoms; heteroarylalkyl having 5 or 6 ring atoms;

e) $R_6$ is —$SiR_{12}R_{13}R_{14}$;

Among the more preferred compounds of Formula (I) of this invention are those in the subgroups, and pharmaceutically acceptable salts thereof:

a) $R_1$ is —$OR_6$;

$R_2$, $R_3$, and $R_4$ are H;

$R_5$ is selected from H, Na, Li, K,

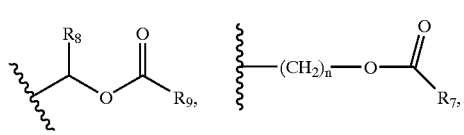

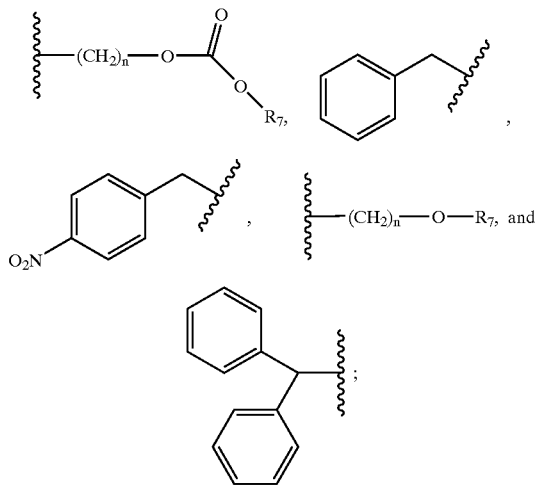
b) $R_2$ is —$OR_6$;
   $R_1$, $R_3$, and $R_4$ are H;
   $R_5$ is selected from H, Na, Li, K,
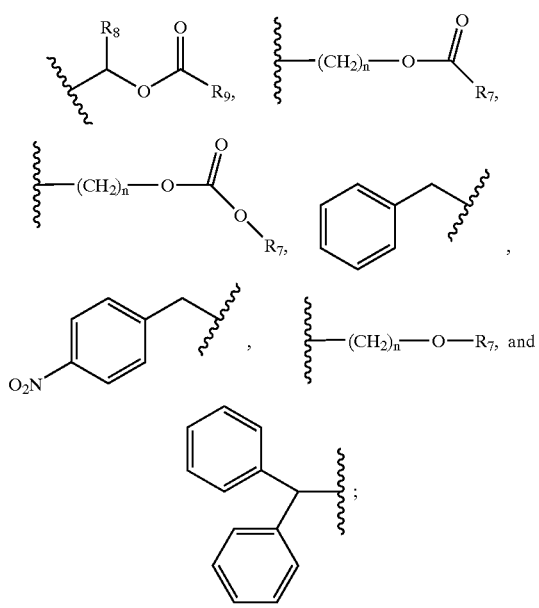
c) $R_3$ is —$OR_6$;
   $R_1$, $R_2$, and $R_4$ are H;
   $R_5$ is selected from H, Na, Li, K,
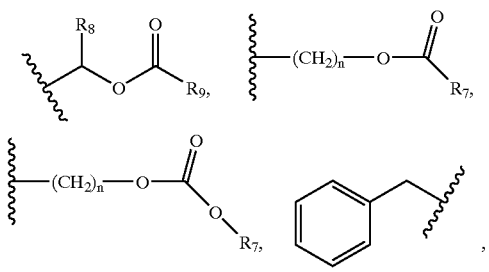
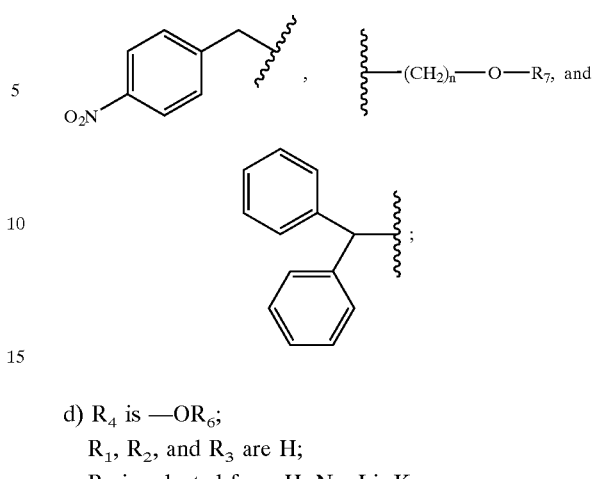
d) $R_4$ is —$OR_6$;
   $R_1$, $R_2$, and $R_3$ are H;
   $R_5$ is selected from H, Na, Li, K,
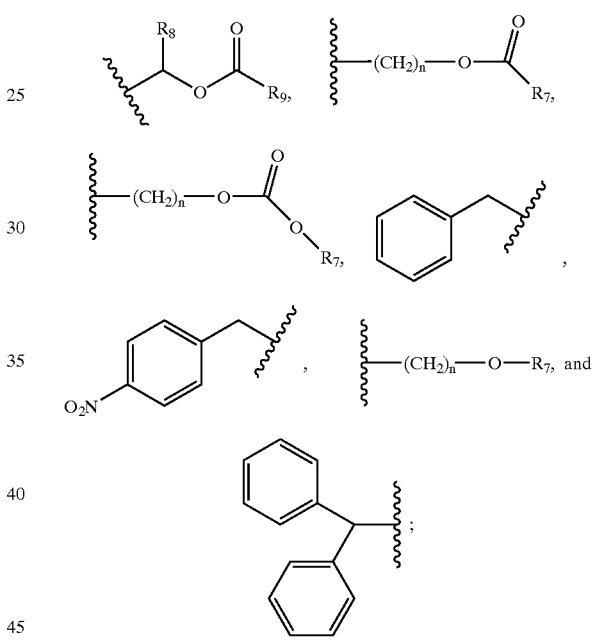
e) $R_5$ is selected from H, Na, Li, K,
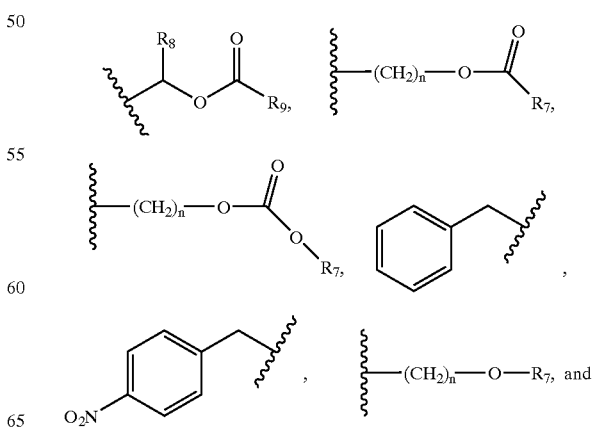

-continued

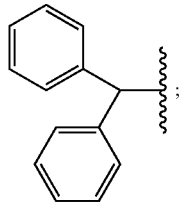

R$_6$ is independently selected from —CH$_3$, —CH$_2$CH$_2$OCH$_3$, —CH$_2$CH$_2$Cl, —CH$_2$CH$_2$N(CH$_3$)$_2$, —cyclohexyl,

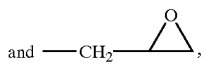

—C(CH$_3$)$_2$CH$_2$CH$_3$, —CH=CHCH$_3$, —CH$_2$(tetrahydrofuran), —CH$_2$CH$_2$OCH$_2$CH$_2$OCH$_2$CH$_3$, —Si(CH$_3$)$_2$t-butyl, —Si(CH$_3$)$_2$phenyl, —Si(CH$_3$)$_2$CH$_2$CH=CH$_2$, —Si(CH$_3$)$_2$CH$_2$CH$_3$, —Si(CH$_3$)$_2$i-propyl, —Si(CH$_3$)$_2$CH=CH$_2$, —Si(CH$_3$)$_2$CH$_2$CH$_2$OCOCH$_3$, —Si(phenyl)$_3$, —CH$_2$CH=CH$_2$, —t-butyl, —CH(phenyl)$_2$, —SiMe$_2$(cyclohexyl), furanyl, pyrazolyl, thienyl, dihydroindolyl, dihydrooxazolyl, dihydropyrimidinyl, benzofuranyl, imidazolyl, pyridyl, tetrazolyl, triazolyl, piperazinyl, indolyl, oxazolyl, piperidinyl, dihydrobenzimidazolyl, tetrahydrofuranyl, benzoxazolyl, isooxazolyl, pyrrolyl, dihydrotriazolyl, and tetrahydrothienyl;

f) R$_5$ is selected from H, Na, Li, K,

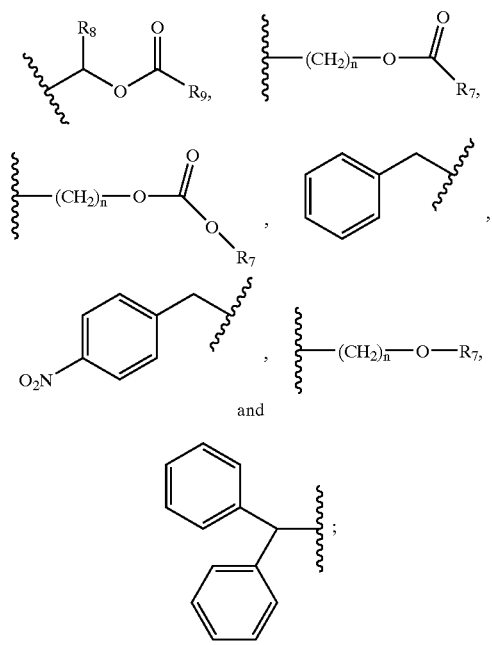

R$_1$, R$_2$, R$_3$ and R$_4$ is independently selected from H, —O-cycloalkyl, —O-alkyl, —O-alkenyl and —O-alkenyl and —OSiR$_{12}$R$_{13}$R$_{14}$;
R$_{12}$, R$_{13}$, and R$_{14}$ are independently selected from alkyl;
provided that three of R$_1$, R$_2$, R$_3$ and R$_4$ are independently hydrogen.

g) R$_5$ is selected from H, Na, Li, and K;

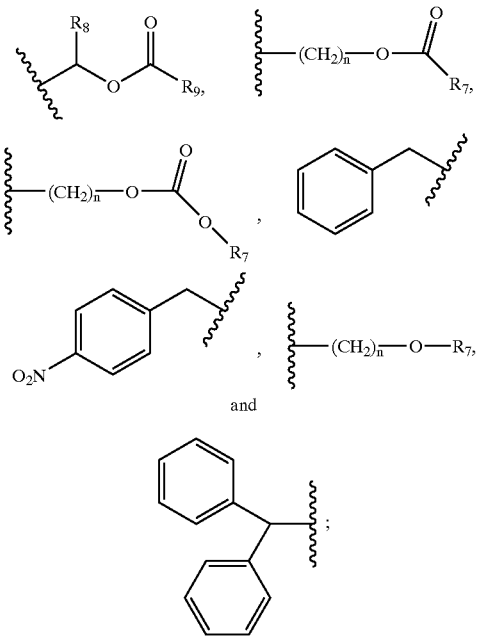

R$_1$, R$_2$, R$_3$ and R$_4$ is independently selected from H, —O-cycloalkyl, —O-alkyl, and —O-alkenyl;
provided that three of R$_1$, R$_2$, R$_3$ and R$_4$ are independently hydrogen.

h) R$_5$ is selected from H, Na, Li, and K;
R$_1$, R$_2$, R$_3$ and R$_4$ are independently selected from H, and —OSiR$_{12}$R$_{13}$R$_{14}$;
R$_{12}$, R$_{13}$, and R$_{14}$ are independently selected from alkyl;
provided that three of R$_1$, R$_2$, R$_3$ and R$_4$ are independently hydrogen.

i) R$_5$ is selected from H, Na, Li, and K;
R$_1$, R$_2$, R$_3$ and R$_4$ is independently selected from H, —O-cycloalkyl, —O-alkyl, and —O-alkenyl;
provided that three of R$_1$, R$_2$, R$_3$ and R$_4$ are independently hydrogen.

Specifically preferred compounds of this invention according to general Formula (I) are the following compounds or pharmaceutically acceptable salts thereof:
(2S,5R)-2-(Diphenylmethoxy)-3,3-dimethyl-7-oxospiro[cyclopropane-1,6-[4]thia[1]azabicyclo[3.2.0]-heptane]-2-carboxylic acid, diphenylmethyl ester,4,4-dioxide,
(1S,2S,5R)-2-tert-Butoxy-3,3-dimethyl-7-oxospiro[cyclopropane-1,6-[4]thia[1]azabicyclo[3.2.0]-heptane]-2-carboxylic acid, diphenylmethyl ester, 4,4-dioxide (Isomer A),
(1R, 2S,5R)-2-tert-butoxy-3,3-dimethyl-7-oxospiro[cyclopropane-1,6-[4]thia[i]azabicyclo[3.2.0]heptane]-2-carboxylic acid, diphenylmethyl ester, 4,4-dioxide (Isomer B),
(2S,5R)-2-tert-butoxy-3,3-dimethyl-7-oxospiro [cyclopropane-1,6-[4]thia[1]azabicyclo[3.2.0]heptane]-2-carboxylic acid, diphenylmethyl ester, 4,4-dioxide (Isomer C),
(1S,2S,5R)-2-[(tert-Butyldimethylsilyl)oxy]-3,3-dimethyl-7-oxospiro [cyclopropane-1,6-[4]thia[1]azabicyclo[3.2.0]-heptane]-2-carboxylic acid, diphenylmethyl ester, 4,4-dioxide, (Isomer A),
(1R, 2S,5R)-2-[(tert-Butyldimethylsilyl)oxy]-3,3-dimethyl-7-oxospiro[cyclopropane-1,6-[4]thia[1]azabicyclo

[3.2.0]-heptane]-2-carboxylic acid, diphenylmethyl ester, 4,4-dioxide (Isomer B),
(2S,5R)-2-[(tert-Butyldimethyl silyl)oxy]-3,3-dimethyl-7-oxospiro[cyclopropane-1,6-[4]thia[1]azabicyclo[3.2.0]-heptane]-2-carboxylic acid, diphenylmethyl ester, 4,4-dioxide (Isomer C),
(1S,2S,5R)-3,3-Dimethyl-7-oxo-2-(2-propenyloxy)spiro-[cyclopropane-1,6-[4]thia[1]azabicyclo[3.2.0]heptane]-2-carboxylic acid, diphenylmethyl ester, 4,4-dioxide, (Isomer A),
(1R, 2S,5R)-3,3-Dimethyl-7-oxo-2-(2-propenyl-oxy)spiro [cyclopropane-1,6-[4]thia[1]azabicyclo[3.2.0]heptane]-2-carboxylic acid, diphenylmethyl ester, 4,4,-dioxide (Isomer B),
(1S,2S,5R)-2-[(tert-Butyldimethylsilyl)oxy]-3,3-dimethyl-7-oxospiro[cyclopropane-1,6-[4]thia[1]azabicyclo [3.2.0]-heptane]-2-carboxylic acid, sodium salt, 4,4-dioxide,
(1R,2S,5R)-2-[(tert-Butyldimethylsilyl)oxy]-3,3-dimethyl-7-oxospiro[cyclopropane-1,6-[4]thia[1]azabicyclo [3.2.0]-heptane]-2-carboxylic acid, sodium salt, 4,4-dioxide,
(2S,5R)-2-[(tert-Butyldimethylsilyl)oxy]-3,3-dimethyl-7-oxospiro[cyclopropane-1,6-[4]thia[1]azabicyclo[3.2.0]-heptane]-2-carboxylic acid, sodium salt, 4,4-dioxide,
(1S,2S,5R)-2-cyclohexyloxy-3,3-dimethyl-7-oxospiro [cyclo-propane-1,6-[4]thia[1]azabicyclo[3.2.0]heptane]-2-carboxylic acid,diphenyl methyl ester, 4.4-dioxide (Isomer A),
(1R, 2S,5R)-2-cyclohexyloxy-3,3-dimethyl-7-oxospiro [cyclo-propane-1,6-[4]thia[1]azabicyclo[3.2.0]-heptane]-2-carboxylic acid,diphenyl methyl ester, 4.4-dioxide (Isomer B)
(2S,5R)-2-cyclohexyloxy-3,3-dimethyl-7-oxospiro[cyclo-propane-1,6-[4]thia[1]azabicyclo[3.2.0]heptane]-2-carboxylic acid,diphenyl methyl ester, 4.4-dioxide (Isomer C),
(1S,2S,5R)-2-cyclohexyloxy-3,3-dimethyl-7-oxospiro [cyclo-propane-1,6-[4]thia[1]azabicyclo[3.2.0]heptane]-2-carboxylic acid, sodium salt, 4.4-dioxide,
(1R, 2S,5R)-2-cyclohexyloxy-3,3-dimethyl-7-oxospiro [cyclo-propane-1,6-[4]thia[1]azabicyclo[3.2.0]heptane]-2-carboxylic acid, sodium salt, 4.4-dioxide,
(2S,5R)-2-cyclohexyloxy-3,3-dimethyl-7-oxospiro[cyclo-propane-1,6-[4]thia[1]azabicyclo[3.2.0]heptane]-2-carboxylic acid, sodium salt, 4.4-dioxide and
(2S,5R)-2-cyclohexyloxy-3,3-dimethyl-7-oxospiro[cyclo-propane-1,6-[4]thia[1]azabicyclo[3.2.0]heptane]-2-carboxylic acid, sodium salt, 4.4-dioxide.

Also included in the present invention are compounds of Formula (II) useful as intermediates for producing compounds of Formula (I).

Formula (II)

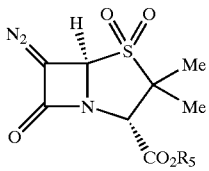

wherein:
$R_5$ is selected from hydrogen, an alkali metal cation, an alkaline earth metal cation, ammonium and tetraalkylammonium, alkyl of 1 to 12 carbon atoms, cycloalkyl of 3 to 10 carbon atoms, alkenyl of 2 to 12 carbon atoms, aralkyl of 7 to 20 carbon atoms, aryl of 6 to 12 carbon atoms and moieties of the formulae:

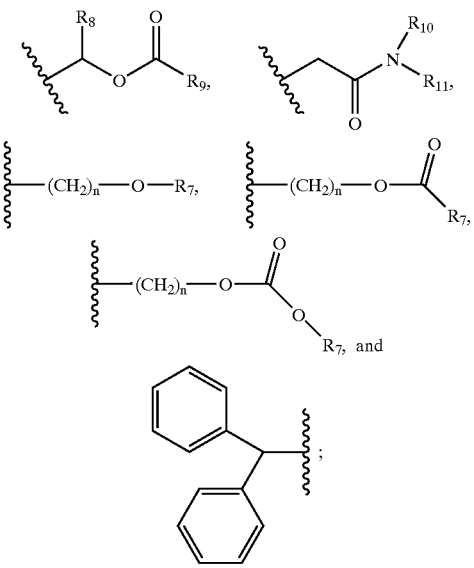

n is an integer of 1 to 3;
$R_7$ is selected from alkyl of 1 to 12 carbon atoms; cycloalkyl of 3 to 10 carbon atoms; aralkyl of 7 to 20 carbon atoms; and aryl of 6 to 12 carbon atoms;
$R_8$, $R_9$, $R_{10}$ and $R_{11}$ are independently selected from alkyl of 1 to 12 carbon atoms;
or a pharmaceutically acceptable salt thereof.

It is understood that the definition of compounds of Formula (I) and (II) when $R_1$, $R_2$, $R_3$, $R_4$, $R_5$, $R_6$, $R_7$, $R_8$, $R_9$, and $R_{10}$, $R_{11}$, $R_{12}$, $R_{13}$, and $R_{14}$ contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of Formula (I) and (II). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where moieties of Formula (I) contain a carboxyl group, salts of the compounds in this invention may be formed with bases such as alkali metal cations (Na, K, Li) or alkaline earth metal cations (Ca or Mg).

For the compounds of Formula (I) defined above and referred to herein, unless otherwise noted, the following terms are defined:

Alkyl as used herein means a branched or straight chain having from 1 to 12 carbon atoms and more preferably from 1 to 6 carbon atoms. Exemplary alkyl groups include methyl, ethyl, propyl, isopropyl, butyl, isobutyl, t-butyl, pentyl and hexyl.

Alkenyl as used herein means a branched or straight chain having from 2 to 12 carbon atoms and more preferably from 2 to 6 carbon atoms, the carbon chain containing at least one carbon-carbon double bond optionally substituted with alkyl of 1 to 12 carbon atoms. Alkenyl, may be used synonymously with the term olefin and includes alkylidenes. Exemplary alkenyl groups include ethylene, propylene and isobutylene.

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Aryl as used herein means a mono or bicyclic aromatic ring having from 6 to 12 carbon atoms. Monocyclic rings preferably have 6 or 7 members and bicyclic rings preferably have 8, 9 or 10 membered ring structures. Exemplary aryl groups include phenyl and naphthyl. The aryl group may be optionally substituted with one or more substituents. Substituted aryl groups preferably have one to three substituents which may include alkyl, alkoxy, perhaloalkyl, halogen, nitro, hydroxy, amino, carboxy, carboxyalkyl, alkylamino, and dialkylamino.

Aralkyl as used herein means an aryl-alkyl group of 7 to 20 carbon atoms in which the aryl and alkyl group are previously defined. Exemplary aralkyl groups include benzyl and phenethyl.

Alkanoyl as used herein refers to —C(O)R where R is alkyl as previously defined.

Bicyclic heteroaryl as used herein refers to fused bicyclic rings having 8 to 20 ring atoms containing 1 to 3 heteroatoms which may be the same or different independently selected from nitrogen, oxygen and sulfur optionally substituted with 1 to 3 substituents which may be the same or different, independently selected from alkyl of 1 to 12 carbon atoms, alkoxy of 1 to 12 carbon atoms, —CN, —$NO_2$, and halogen.

Cycloalkyl as used herein means a saturated ring having from 3 to 10 carbon atoms and more preferably from 3 to 6 carbon atoms which may be optionally substituted with up to three substituents independently selected from halogen, —OH, and —$NH_2$. Exemplary cycloalkyl rings include cyclopropyl, cyclobutyl, cyclopentyl and cyclohexyl.

Halogen as used herein means chloro, fluoro, bromo and iodo.

Haloalkyl as used herein refers to an alkyl group, as defined above, in which one or more hydrogen atoms are replaced with a halogen. Perhaloalkyl refers to alkyl groups in which each of the hydrogens are replaced with halogen atoms. Exemplary haloalkyl groups include chloromethyl, dibromomethyl, and the perhaloalkyl, trifluoromethyl.

Heteroarylalkyl as used herein refers to a monocyclic ring having 5 or 6 ring atoms containing 1 to 3 heteroatoms which may be the same or different, independently selected from nitrogen, oxygen and sulfur, optionally substituted with 1 to 3 substituents which may be the same or different independently selected from alkyl of 1 to 12 carbon atoms, alkoxy of 1 to 12 carbon atoms, —CN, —$NO_2$, and halogen and bonded to an alkyl moiety as previously defined having 1 to 12 carbon atoms. Exemplary heteroarylalkyl groups include 2-,3- and 4-picolyl.

Heteroaryl as use herein refers to a monocyclic ring having 5 or 6 ring atoms containing 1 to 3 heteroatoms which may be the same or different, independently selected from nitrogen, oxygen and sulfur, optionally substituted with 1 to 3 substituents which may be the same or different independently selected from alkyl of 1 to 12 carbon atoms, alkoxy of 1 to 12 carbon atoms, —CN, —$NO_2$, and halogen.

Alkyloxacyclopropyl as used herein refers to an alkyl group, as defined above, bonded to a cyclopropyl ring in which one of the carbon atoms is replaced with an oxygen atom.

Phenyl as used herein refers to a 6-membered aromatic ring.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, perhaloalkoxy refers to an alkoxy group, as defined above, in which each hydrogen atom of the alkyl group has been replaced by a halogen.

Standard Pharmacological Test Procedures

Representative compounds of the invention were tested in standard pharmacological test procedures against the commercially available inhibitors, clavulanic acid, sulbactam, and tazobactam to evaluate inhibition of the class A(TEM-1) and class C(AmpC) beta-lactamase enzymes. $IC_{50}$ values are determined spectrophotometrically using a 10-minute preincubation of enzyme with the inhibitor at 25° C. before addition of nitrocefin as the substrate(100 mg/mL). The results are shown in Table I.

TABLE I

| | $IC_{50}$ (nM) | | |
|---|---|---|---|
| Example # | Class C(AmpC) | Class A(TEM-1) | Class B(Imi-1) |
| 8 | 1,900 | 17,000 | >240,000 |
| 9 | 21 | 650 | 12,000 |
| 10 | 343 | 12,000 | >240,000 |
| 12 | 32,000 | 1,700 | 30,000 |
| 13 | 37 | 510 | 4,000 |
| 14 | 3,160 | 130,000 | 132,000 |
| Sulbactam | 65,900 | 1,400 | — |
| Tazobactam | 47,700 | 60 | — |

As shown in Table I, the compounds of Example 9, 10, and 13 are very potent inhibitors of class C(AmpC) enzymes. Example 9 and 13 are also potent inhibitors against class A(TEM-1) enzymes. Both Examples 9 and 13 are inhibitors of class C enzymes.

Representative Example 9 was tested in a microbial assay in combination with the penicillin antibiotic Piperacillin. In these tests, minimum inhibitory concentration(MIC) are determined in broth using serial two-fold dilutions with a 1:1 ratio of Piperacillin to inhibitor(N. A. Kuck; N. V. Jacobs; P. J. Peterson; W. J. Weiss; and R. T. Testa, in "Antimicrobial Agents and Chemotherapy", Vol. 33, 1989, pages 1964–1969).

TABLE II

| | MIC (ug/mL) | | | |
|---|---|---|---|---|
| | Piperacillin | Piperacillin + Example 9 | Cefotaxime | Cefotoxime + Example 9 |
| E. coli + (TEM-1) | >64 | 64 | <0.06 | <0.06 |
| E. coli + (AmpC) | >64 | 32 | >64 | 16 |
| E. coli 300 + (AmpC) | 32 | 0.5 | 16 | 0.5 |
| P. aeroginosa (AmpC derepressed) | >64 | 8 | >64 | 16 |
| S. marcescens (AmpC) | 32 | 8 | 8 | 4 |
| E. coli GC 6265 (TEM-1) | >64 | <0.06 | 64 | <0.06 |

TABLE III

| | MIC (ug/mL) | | | |
|---|---|---|---|---|
| | Piperacillin | Piperacillin + Example 12 | Piperacillin + Example 13 | Piperacillin + Example 14 |
| E. coli + (TEM-1) | >64 | >64 | >64 | >64 |
| E. coli + (AmpC) | 32 | 16 | 4 | 16 |
| E. coli 300 + (AmpC) | 32 | 6 | 4 | 16 |
| P. aeroginosa | >64 | 64 | 32 | 64 |
| S. marcescens (AmpC) | 64 | 64 | 32 | 64 |
| E. coli GC 6265 (TEM-1) | >64 | >64 | 64 | >64 |

Referring to Table II, piperacillin when combined with Example 9 shows increased microbiological activity in microorganisms containing beta-lactamase enzymes, TEM-1 and AmpC. Similar results are shown when the combination of Example 9 and cefotaxime was used, where the antimicrobial activity against the same strains was also increased. In particular, Example 9 shows very potent activity as a beta-lactamase inhibitor with E.coli strains[E.coli 300+(AmpC) and E.coli GC6265 (TEM-1)].

When the compounds are employed for the above utility, they may be combined with one or more pharmaceutically acceptable carriers, for example, solvents, diluents and the like, and may be administered parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, preferably given in divided doses two to four times daily or in a sustained release form. For most large mammals, the total daily dosage is from about 1 to 1000 mg, preferably from about 2 to 500 mg. Dosage forms suitable for internal use comprised from about 0.5 to 1000 mg of the active compound in intimate admixture with a liquid pharmaceutically acceptable carrier. This dosage regime may be adjusted to provide the optimal therapeutic response. For example, several divided doses may be administered daily or the dose may be proportionally reduced as indicated by the exigencies of the therapeutic situation. A decided practical advantage is that these active compounds may be administered by intravenous, intramuscular or subcutaneous routes. Liquid carriers include sterile water polyethylene glycol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as coloring agents, preserving agents, and antioxidants, for example, vitamin E, ascorbic acid, BHT and BHA.

These active compounds may also be administered parenterally or intraperitoneally. Solutions or suspensions for these active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection use include sterile aqueous solution for dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms such as bacteria and fungi. The carrier can be a solvent or dispersions medium containing, for example, water ethanol, polyol (e.g. glycerol, propylene glycol and liquid polyethylene glycol), suitable mixtures thereof, and vegetable oils.

According to a further aspect of the present invention there is provided a series of compounds of Formula (I) or the pharmaceutically acceptable salts thereof as defined hereinbefore for use in a method of treatment of human or animal disease.

The compounds of this invention may be formulated neat or may be combined with one or more pharmaceutically acceptable carriers for administration. For example, solvents, diluents and the like; and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

The compounds of Formula (I) may be administered admixed with a beta-lactam antibiotic, administered simultaneously with a beta-lactam antibiotic or administered as a separate agent during a course of treatment with a beta-lactam antibiotic.

In some cases it may be desirable to administer the compounds directly to the airways in the form of an aerosol.

DESCRIPTION OF THE PREFERRED EMBODIMENTS

The 6-(spirocyclopropyl)penicillanic acid 4,4-dioxide compounds of the present invention are prepared according to the following reaction Scheme I.

15

Referring to the process of Scheme I, modifying a procedure as described (J. J. Bos, R. Cuperus, R. Wielinga, U.S. Pat. No. 4,695,628), commercially available 6-aminopenicillanic acid 1 was oxidized by treatment with a mixture of potassium permanganate and concentrated sulfuric acid, while cooling at a temperature at or below 0° C. Upon completion of the oxidation, excess potassium permanganate was removed by treatment with a 50% aqueous sodium bisulfite solution followed by the addition of anhydrous ammonia gas, to a pH of 3, with continued cooling to provide 6-aminopenicillanic acid 4,4-dioxide, 2 as a solid.

Again, referring to Scheme I, step 2, 6-aminopenicillanic acid 4,4-dioxide, 2 was reacted with diphenyldiazomethane (Org.Synthesis, Coll. Vol. 3, 35) in a chlorinated solvent which includes methylene chloride at 0° C. or below in the presence of methanol to afford 6-aminopenicillanate 4,4-dioxide hydrochloride, 3 where $R_5$ is diphenylmethyl. The product was isolated as the hydrochloride salt by adding a saturated hydrogen chloride solution in diethyl ether following a similar described procedure (S. A. Matlin, L. Chan, B. Catherwood, J.Chem.Soc., Perkin Trans I, 1990, 89–96). Unreacted starting material was removed by filtration before adding the saturated hydrogen chloride solution in diethyl ether.

While not being bound by theory, it is contemplated that other ester protecting groups other than diphenylmethyl could be synthesized by first reacting 6-aminopenicillanic acid 4,4-dioxide, 2 optionally with the amino group protected with moieties which include but are not limited to t-butoxycarbonyl(BOC), with an excess of halogenating agent which include but are not limited to thionyl chloride and oxalyl chloride followed by treatment with an appropriate alcohol which include but not limited to an alkyl alcohol of 1 to 12 carbon atoms, an aralkyl alcohol of 7 to 20 carbon atoms, a cycloalkyl alcohol of 3 to 10 carbon atoms and an alkenyl alcohol of 2 to 12 carbon atoms to afford 6-aminopenicillanate 4,4-dioxide hydrochloride, 3 with ester functionality hereinbefore defined as $R_5$. Alternatively, esters may be prepared by reaction of 6-aminopenicillanic acid 4,4-dioxide, 2 optionally with the amino group protected with moieties which include but are not limited to t-butoxycarbonyl (BOC), with an excess of ester producing reagent $R_5X$ where X is a leaving group which includes but is not limited to halogen, triflate, mesylate, tosylate, methyl sulfamyl, toluene sulfamyl and the like and where $R_5$ includes but not limited to an alkyl of 1 to 12 carbon atoms, aralkyl of 7 to 20 carbon atoms, a cycloalkyl of 3 to 10 carbon atoms and alkenyl of 2 to 12 carbon atoms to afford 6-aminopenicillanate 4,4-dioxide hydrochloride, 3.

SCHEME I

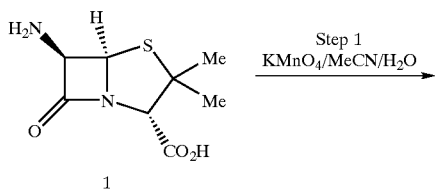

1

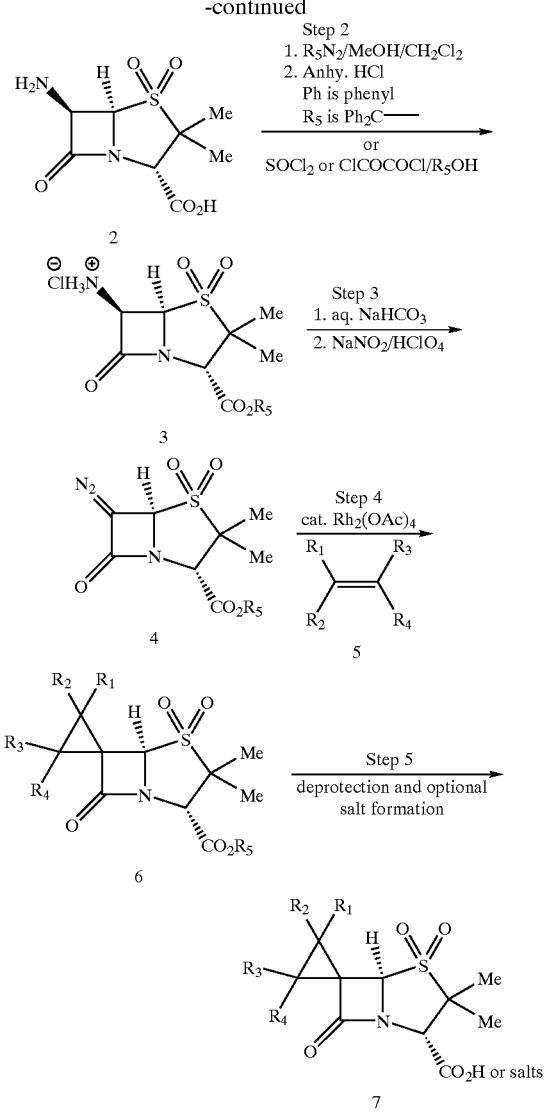

As further described in Scheme I, step 3, 6-diazo-penicillanate 4,4-dioxide 4, was prepared by neutralizing the hydrochloride salt of 6-aminopenicillanate 4,4-dioxide hydrochloride 3, with a saturated aqueous solution of sodium bicarbonate followed by treating the resulting free amine in a biphasic mixture containing an organic solvent, preferably methylene chloride and water with sodium nitrite and iN perchloric acid solution. The 1N perchloric acid solution wa s added portionwise while maintaining the temperature, preferably at –10 to 0° C. The product was isolated from the separated organic layer.

As further described in Scheme I, step 4, insertion reaction between 6-diazo-penicillanate 4,4-dioxide 4, and olefin 5 wherein $R_1$, $R_2$, $R_3$, $R_4$ are hereinbefore defined, in the presence of a copper or rhodium catalyst, preferably a rhodium catalyst and most preferably rhodium acetate, to provide 7-oxospiro(cyclopropane)penicillanate 4,4-dioxide 6 as a mixture of isomers. The copper or rhodium catalyst have attached chiral and nonchiral ligands which include but are not limited to acetate, octanoate, acetylacetonate, trifluoroacetate, and the like. Typically, the insertion reaction was carried out at room temperature in an organic solvent, which include but are not limited to benzene and methylene chloride in the presence of excess olefin 5. When two or more stereoisomers were obtained the isomers were separated by chromatography.

Once again referring to Scheme I, step 5, the ester protection at $R_5$ of 7-oxospiro(cyclopropane)penicillanate 4,4-dioxide 6, may be removed to give the corresponding 7-oxospiro(cyclopropane)penicillanic-2-carboxylic acid 4,4-dioxide 7 by conventional procedures such as hydrolysis, solvolysis, chemical reduction, or hydrogenolysis. Where an ester grouping such as p-nitrobenzyl, benzyl or diphenylmethyl was used catalytic hydrogenolysis in a suitable solvent system can be used. Suitable solvent systems include ethyl acetate-water-sodium bicarbonate, water-ethanol-methanol, ethyl acetate, tetrahydrofuran-aqueous dipotassium hydrogenphosphate-isopropanol and the like. Treatment under hydrogen pressures of 1 to 4 atmospheres in the presence of a hydrogenation catalyst such as palladium on charcoal, palladium hydroxide, platinum oxide or the like at temperatures ranging from 0° C. to 40° C. for 1 to 4 hours affords the free carboxylic acid. Similarly, conventional carboxyl acid protecting groups may be removed by methods known to those skilled in the art. Depending on the carboxyl protecting group, the method of deprotection, as described above, will vary. Product isolation from the deprotection step again varies based on the method used, but all methods used in this transformation follow conventional techniques in the art including chromatography and lyophilization.

It is usual to isolate the 6(spirocyclopropyl)penicillanic acid 4,4-dioxides of Formula (I) as an alkali metal salt wherein $R_5$ is a lithium, sodium or potassium ion or as a water soluble zwitterionic species including ammonium and tetraalkylammonium.

Compounds of Formula (I) wherein $R_5$ is a physiologically hydrolyzable ester which include acetoxymethyl, pivaloyloxymethyl, methoxymethyl, and the like, may be administered directly to the host without deblocking since such hydrolyzable esters are hydrolyzed in vivo under physiological conditions. The physiologically hydrolyzable esters may be prepared by methods known to those skilled in the art.

Reactions of Scheme I are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have centers of asymmetry. The compounds may, therefore, exist in at least two and often more stereoisomeric forms. The present invention encompasses all stereoisomeric forms of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

The invention will be more fully described in conjunction with the following specific examples which are not to be construed as limiting the scope of the invention.

EXAMPLE 1

(2S,5R,6S)-6-Amino-3,3-dimethyl-7-oxo-4-thia-1-azabicyclo-[3.2.0]heptane-2-carboxylic acid 4,4-dioxide To a 0° C. solution of 6-aminopenicillanic acid (10.0 g, 0.046 mol) in a mixture of water (32 mL) and acetonitrile(48 mL) was added, dropwise, a solution containing potassium permanganate (9.6 g, 0.061 mol) and concentrated sulfuric acid (6 mL) in water (120 mL). At the end of the addition, a 50% aqueous sodium bisulfite solution was added, dropwise, to the reaction mixture until a clear solution was observed. Anhydrous ammonia gas was passed through the solution at 0° C. until pH 3, at which time the sulfone product precipitated. The solid was filtered, washed with acetone and dried in vacuo to obtain 9.0 g(78%) of the desired product.

IR(DMSO): 3600, 1614, 1583, 1391, 1314, 1200, 1119 cm$^{-1}$;

$^1$H NMR(300 MHz, DMSO-d$_6$): δ1.34(s,3H), 1.44(s,3H) 3.34(br,3H), 4.25(s,1H), 4.87(d,1H,j=4.5 Hz), 4.24(d,1H,J= 4.5 Hz);

$^{13}$C NMR(75 MHz, DMSO-d$_6$): δ17.0, 19.4, 62.7, 62.8, 63.8, 66.6, 168.3, 179.3;

HRMS ($C_8H_{12}N_2O_5S$): Calcd. 249.0545, Found 249.0537 (M+H).

EXAMPLE 2

(2S,5R,6S)-6-Amino-3,3-dimethyl-7-oxo-4-thia-1-azabicyclo[3.2.0]heptane-2-carboxylic acid, diphenylmethyl ester, hydrochloride salt, 4,4-dioxide To a 0° C. suspension of 6-aminopenicillanic acid sulfone (7.0 g, 0.028 mol) in methanol (21 mL) was added, portionswise, a solution of diphenyldiazomethane(5.5 g, 0.028 mol) in methylene chloride (50 mL). The resultant mixture was stirred for about 1 hour by which time the formed purple color was dissipated. Diethyl ether was added and the reaction mixture was filtered to remove unreacted 6-aminopenicillanic acid (1.0 g). The filtrate was cooled in an ice bath and a saturated solution of anhydrous hydrogen chloride in diethyl ether. was added, dropwise, until a thick precipitate was obtained. The solid was filtered, washed with diethyl ether several times and dried to obtain 8.0 g of the desired product (73%).

IR(DMSO): 2962, 1803, 1755, 1495, 1322, 1209, 1156, 1081 cm$^{-1}$;

$^1$H NMR(300 MHz, acetone-d$_6$): δ1.24 (s,3H), 1.62 (s,3H), 3.74(br,3H), 4.86(s,1H), 5.42(br,1H), 5.54(br,1H), 7.02(s,1H), and 7.32–7.53(m,10H);

MS(Electrospray): m/z 414.9 (M+H).

EXAMPLE 3

(2S,5R)-6-Diazo-3,3-dimethyl-7-oxo-4-thia-1-azabicyclo-[3.2.0]heptane-2-carboxylic acid, diphenylmethyl ester, 4,4-dioxide The product of Example 2 (4.7 g, 0.01 mol) was neutralized with a 5% aqueous sodium bicarbonate solution and extracted with methylene chloride. The organic layer was added to the reaction flask and additional methylene chloride was added (total volume 400 mL). The reaction mixture was cooled in an ice bath and a solution of sodium nitrite (1.65 g, 0.024) in water(400 mL) was added. The resulting biphasic mixture was stirred vigorously while in perchloric acid (22.5 mL) solution was added portionwise. The resulting mixture was stirred for 2 hours at 0° C. and the organic layer was separated, washed with brine, water and dried. Removal of the solvent gave 4 g (90%) of the desired product.

IR(CDCl$_3$): 2106, 1774, 1325, 1237, 1210 cm$^{-1}$;

$^1$H NMR(300 MHz, CDCl$_3$): δ1.17(s,3H), 1.58(s,3H), 4.33(s,1H), 5.40(s,1H), 6.99(s,1H), and 7.35(m,10H);

¹³C NMR(75 MHz, CDCl₃): δ19.4, 19.5, 62.7, 65.2, 68.8, 79.2, 126.9, 127.6, 127.8, 128.3, 128.4, 128.7, 128.8, 138.6, 138.9, 165.2, and 166.0;

MS(Electrospray): m/z 425.9 (M+H).

General Procedure for the Insertion Reaction (Step 4)

To a room temperature solution of the olefin (2 equivalents) in methylene chloride (0.2–0.4M) was added a catalytic amount of rhodium acetate followed by a dropwise addition of a solution of the 6-diazopenicillin sulfone (1 equivalent) in methylene chloride (0.2M). The resulting mixture was stirred for from 15 minutes to 2 hours and the solvent was removed in vacuo. The crude product was purified by silica gel chromatography.

General Procedure for the Deprotection of Diphenylmethyl Ester and the Preparation of the Corresponding Salt (Step 5)

To a solution of ester in ethyl acetate (0.2M) was added 10% palladium-carbon (20% wt. of ester) and the resultant heterogeneous mixture was hydrogenated using a Parr hydrogenation apparatus (45 lb/sq.ft.) for from 2 to 5 hours. The reaction mixture was filtered and the solvent was removed in vacuo. The acid was dissolved in water and an equimolar amount of solid sodium bicarbonate was added. The resultant mixture was stirred for from 2 to 4 hours at room temperature and extracted with ethyl acetate. The aqueous layer was lyophilized to obtain the sodium salt.

EXAMPLE 4

(2S,5R)-2-(Diphenylmethoxy)-3,3-dimethyl-7-oxospiro[cyclopropane-1,6-[4]thia[1]azabicyclo [3.2.0]-heptane]-2-carboxylic acid, diphenylmethyl ester,4,4-dioxide The general procedure was followed for the insertion reaction (step 4) using 6-diazo penicillanic acid sulfone diphenylmethyl ester (300 mg, 0.71 mmol) and diphenymethyl vinyl ether (296 mg, 1.41 mmol) to obtain the product (241 mg, 56%) as a mixture of isomers(56%). Pure Isomer A (120 mg) was obtained by column chromatography (Silica Gel: hexane gradient to 30% ethyl acetate/hexane). Isomer B was not isolated and characterized.
Isomer A
IR(CDCl₃): 2873, 1797, 1758, 1324, 1179, 1118, 699 cm⁻¹;
¹H NMR(300 MHz, CDCl₃): δ1.08(s,3H), 1.55(s,3H), 1.68(m,1H), 1.83(m,1H), 3.92(m,1H), 4.33(s,1H), 4.41(s,1H), 5.51(s,1H), 6.99(s,1H), and 7.27–7.38(m,20H);
¹³C NMR(75 MHz, CDCl₃): δ16.4, 18.3, 19.5, 38.3, 57.0, 63.2, 64.3, 66.3, 78.9, 84.7, 126.8, 126.9, 127.4, 127.7, 127.9, 128.3, 128.4, 128.5, 128.7, 128.8, 138.7, 138.9, 140.4, 140.6, 166.3, and 176.1;
HRMS (C₃₆H₃₃NO₆S) Calcd. 608.2107, Found 608.2154 (M+H).

EXAMPLE 5

(1S,2S,5R)-2-tert-Butoxy-3,3-dimethyl-7-oxospiro [cyclo-propane-1,6-[4]thia[1]azabicyclo[3.2.0]-heptane]-2-carboxylic acid, diphenylmethyl ester, 4,4-dioxide (Isomer A), (1R, 2S,5R)-2-tert-butoxy-3,3-dimethyl-7-oxospiro [cyclo-propane-1,6-[4]thia[1]azabicyclo[3.2.0] heptane]-2-carboxylic acid, diphenylmethyl ester, 4,4-dioxide (Isomer B) and (2S,5R)-2-tert-butoxy-3,3-dimethyl-7-oxospiro [cyclopropane-1,6-[4]thia[1]azabicyclo[3.2.0] heptane]-2-carboxylic acid, diphenylmethyl ester, 4, 4-dioxide (Isomer C)

The general procedure was followed for the insertion reaction (step 4) using 6-diazo penicillanic acid sulfone diphenylmethyl ester(660 mg, 1.55 mmol) and t-butylvinyl ether(300 mg, 3.0 mmol) to obtain the product (424 mg, 55%) as a mixture of 3 isomers(55%). Pure Isomer A (170 mg), Isomer B (160 mg) and Isomer C (94 mg) were obtained by column chromatography (Silica Gel: hexane gradient to 30% ethyl acetate/hexane).
Isomer A
IR(CDCl₃) 2976, 1797, 1759, 1323, 1260, 1173, 1118, 701 cm⁻¹;
¹H NMR(300 MHz, CDCl₃): δ1.14(s,3H), 1.26(s,9H), 1.57(s,3H), 1.66–1.77(m,2H), 3.85(m,1H), 4.42(s,1H), 4.59 (s,1H), 6.97(s,1H), 7.29–7.40(m,10H);
¹³C NMR(75 MHz, CDCl₃): δ17.3, 18.6, 19.7, 27.9, 37.5, 52.2, 63.2, 64.3, 66.6, 78.9, 126.8, 127.7, 128.3, 128.7, 128.8, 139.1, 139.4, 166.8, 177.4;
MS(Electrospray): m/z 498.0 (M+H).
Isomer B
IR(CDCl₃): 2975, 1800, 1754, 1329, 1180, 1171, 940, 702 cm⁻¹;
¹H NMR(300 MHz, CDCl₃): δ1.09(s,3H), 1.26(s,9H), 1.50(m,1H), 1.56(s,3H), 1.71(m,1H), 3.96(m,1H), 4.48(s,1H), 4.72(s,1H), 7.00(s,1H), 7.30–7.40(m,10H);
¹³C NMR(75 MHz, CDCl₃): δ17.7, 19.5, 20.5, 27.8, 37.4, 52.6, 63.0, 63.4, 68.2, 78.8, 126.8, 127.9, 128.3, 128.7, 128.8, 138.7, 139.0, 166.7, 176.7;
HRMS (C₂₇H₃₁NO₆S): Calcd. 498.1950, Found 498.1942 (M+H).
Isomer C
IR(CDCl₃): 2975, 1798, 1744, 1321, 1175, 1118, 700 cm⁻¹;
¹H NMR(300 MHz, CDCl₃): δ1.27(s,3H), 1.28(s,9H), 1.56(s,3H), 1.86(m,2H), 3.81(m,1H), 4.50(s,1H), 4.56(s,1H), 6.94(s,1H), 7.31–7.36(m,10H);
MS(Electrospray): m/z 498.0 (M+H).

EXAMPLE 6

(1S,2S,5R)-2-[(tert-Butyldimethyl silyl)oxy]-3,3-dimethyl-7-oxospiro[cyclopropane-1,6-[4]thia[1]azabicyclo [3.2.0]-heptane]-2-carboxylic acid, diphenylmethyl ester, 4,4-dioxide, (Isomer A)

(1R,2S,5R)-2-[(tert-Butyldimethyl silyl)oxy]-3,3-dimethyl-7-oxospiro[cyclopropane-1,6-[4]thia[1] azabicyclo[3.2.0]-heptane]-2-carboxylic acid, diphenylmethyl ester, 4,4-dioxide (Isomer B) and (2S,5R)-2-[(tert-Butyldimethyl silyl)oxy]-3,3-dimethyl-7-oxospiro[cyclopropane-1,6-[4]thia[1] azabicyclo[3.2.0]-heptane]-2-carboxylic acid, diphenylmethyl ester, 4,4-dioxide (Isomer C)

The general procedure was followed for the insertion reaction (step 4) using 6-diazo penicillanic acid sulfone diphenylmethyl ester(1 g, 2.4 mmol) and t-butyldimethylsilyl vinyl ether(760 mg, 4.8 mmol) to obtain the product (700 mg, 54%) as a mixture of 3 isomers. Pure Isomer A (280 mg), Isomer B (275 mg) and Isomer C (120 mg) were obtained by column chromatography (Silica Gel: hexane gradient to 10% ethyl acetate).
Isomer A
IR(CDCl₃): 2956, 1799, 1760, 1325, 1260, 1179, 1118, 1015, 840, 700 cm⁻¹;
¹H NMR(300 MHz, CDCl₃): δ0.10(s,3H), 0.11 (s,3H), 0.90(s,9H), 1.14(s,3H), 1.58(s,3H), 1.67–1.74(m,2H), 4.01 (dd,1H,J=4.5 and 3.9 Hz), 4.45(s,1H), 4.55(s,1H), 6.99(s,1H), 7.29–7.38(m,10H);
¹³C NMR(75 MHz, CDCl₃): δ0.0, 1.0, 18.0, 18.3, 18.5, 19.6, 25.6, 38.4, 52.8, 63.3, 64.4, 66.2, 79.0, 126.8, 127.8, 128.3, 128.7, 128.8, 138.7, 139.0, 166.5, 176.8;

HRMS (C$_{29}$H$_{37}$NO$_6$SSi) Calcd. 556.2189, Found 556.2206 M+H).

Isomer B

IR(CDCl$_3$): 2958, 1798, 1755, 1324, 1181, 1111, 939, 837 cm$^{-1}$;

$^1$H NMR(300 MHz, CDCl$_3$): δ0.10(s,3H), 0.11(s,3H), 0.90(s,9H), 1.10(s,3H), 1.50(dd,1H,J=6.9 and 4.7 Hz), 1.57 (s,3H), 1.70(t,1H,J=6.8 Hz), 4.11(dd,1H,J=6.3 and 4.7 Hz), 4.47(s,1H), 4.70(s,1H), 6.99(s,1H),7.28–7.46(m,10H);

$^{13}$C NMR(75 MHz, CDCl$_3$): δ0.0, 17.8, 18.2, 19.6, 20.0, 25.5, 39.3, 54.2, 63.0, 63.5, 68.2, 78.8, 126.8, 127.8, 128.3, 128.7, 128.8, 138.7, 139.0, 166.7, 176.5;

HRMS (C$_{29}$H$_{37}$NO$_6$SSi) Calcd. 556.2189, Found 556.2214 (M+H).

Isomer C

IR(CDCl$_3$): 2931, 1802, 1759, 1321, 1259, 1182, 1118, 839 cm$^{-1}$;

$^1$H NMR(300 MHz, CDCl$_3$): δ0.11(s,3H), 0.12(s,3H), 0.90(s,9H), 1.12(s,3H), 1.56(s,3H), 1.84(m,2H), 3.95(m,1H), 4.46(s,1H), 4.52(s,1H), 6.97(s,1H), 7.28–7.48(m,10H);

$^{13}$C NMR(75 MHz, CDCl$_3$): δ–4.9, 0.0, 17.9, 18.5, 18.7, 19.6, 25.5, 39.5, 55.7, 63.3, 64.4, 68.4, 78.9, 126.9, 127.6, 128.3, 128.6, 128.7, 128.7, 138.8, 139.0, 166.4, 174.8;

HRMS (C$_{29}$H$_{37}$NO$_6$SSi) Calcd. 556.2189, Found 556.2236 (M+H).

EXAMPLE 7

(1S,2S,5R)-3,3-Dimethyl-7-oxo-2-(2-propenyloxy) spiro[cyclo-propane-1,6-[4]thia[1]azabicyclo[3.2.0] heptane]-2-carboxylic acid, diphenylmethyl ester, 4,4-dioxide, (Isomer A) and (1R,2S,5R)-3,3-Dimethyl-7-oxo-2-(2-propenyloxy) spiro[cyclo-propane-1,6-[4]thia[1]azabicyclo[3.2.0] heptane]-2-carboxylic acid, diphenylmethyl ester, 4,4,-dioxide (Isomer B)

The general procedure was followed for the insertion reaction (step 4) using 6-diazo penicillanic acid sulfone diphenylmethyl ester(200 mg, 0.47 mmol) and allyl vinyl ether(79 mg, 0.94 mmol) to obtain the product (110 mg, 49%) as a mixture of 3 isomers. Pure Isomer A (40 mg) and Isomer B (40 mg) were obtained by column chromatography (Silica Gel: hexane gradient to 15% ethyl acetate). Isomer C was not isolated or characterized.

Isomer A

IR(CDCl$_3$): 2982, 1797, 1756, 1323, 1169, 1118, 701 cm$^{-1}$:

$^1$H NMR(300 MHz, CDCl$_3$): δ1.14(s,3H), 1.58(s,3H), 1.71(dd,1H,J=6.0 and 5.7 Hz), 1.79(dd,1H,J=6.0 and 3.6 Hz), 3.92(dd,1H,J=4.8 and 3.9 Hz), 4.11(m,2H), 4.46(s,1H), 4.63(s,1H), 5.28(m,2H), 5.88(m,1H), 6.98(s,1H), 7.29–7.38 (m,10H);

$^{13}$C NMR(75 MHz, CDCl$_3$): δ16.4, 18.5, 19.6, 38.2, 57.5, 63.3, 64.3, 66.3, 72.3, 79.0, 118.7, 126.8, 127.7, 128.3, 128.7, 128.8, 133.0, 138.7, 138.9, 166.4, 176.2;

MS(Electrospray): m/z 481.9 (M+H).

Isomer B

IR(CDCl$_3$): 1804, 1756, 1331, 1171, 1149, 984, 703 cm$^{-1}$;

$^1$H NMR(300 MHz, CDCl$_3$): δ1.12(s,3H), 1.55–1.60(m, 1H), 1.58(s,3H), 1.70(t,1H,J=5.1 Hz), 4.02(dd,1H,J=5.1 and 3.6 Hz), 4.16(m,1H), 4.27(m,1H), 4.48(s,1H), 5.19(dd,1H, J=6.9 and 1.2 Hz), 5.34(dd,1H,J=11.7 and 1.2 Hz), 5.89(m, 1H), 6.98(s,1H), 7.30–7.39(m,10H);

$^{13}$C NMR(75 MHz, CDCl$_3$): δ17.8, 18.0, 19.5, 38.8, 58.9, 63.0, 63.4, 68.3, 72.2, 78.9, 117.7, 126.8, 127.8, 128.3, 128.7, 128.7, 128.8, 133.4, 138.6, 139.0, 166.6, 175.7;

MS(Electrospray): m/z 482.0 (M+H).

EXAMPLE 8

(1S,2S,5R)-2-[(tert-Butyldimethylsilyl)oxy]-3,3-dimethyl-7-oxospiro[cyclopropane-1,6-[4]thia[1] azabicyclo[3.2.0]-heptane]-2-carboxylic acid, Sodium Salt, 4,4-dioxide The general procedure was followed for the deprotection and salt formation (step 5) using the product of Example 7, Isomer A (50 mg) to give the desired product (20 mg, 54% for 2 steps).

IR(D$_2$O): 3438, 2955, 1768, 1613, 1322, 1193, 1179, 839 cm$^{-1}$; $^1$H NMR(300 MHz, D$_2$O): δ0.10(s,3H), 0.11 (s,3H), 0.91(s,9H), 1.45(s,3H), 1.58(s,3H), 1.78–1.85(m,2H), 4.19 (s,1H), 4.25(dd,1H,J=6.48 and 5.13 Hz), 5.20(s,1H);

$^{13}$C NMR(75 MHz, D$_2$O): δ18.1, 18.3, 20.1, 20.8, 25.7, 39.4, 55.6, 65.6, 69.1, 173.2, 180.8;

HRMS (C$_{16}$H$_{26}$NO$_6$SSi): Calcd. 390.1407, Found 390.1436 (M+H).

EXAMPLE 9

(1R,2S,5R)-2-[(tert-Butyldimethylsilyl)oxy]-3,3-dimethyl-7-oxospiro[cyclopropane-1,6-[4]thia[1] azabicyclo[3.2.0]-heptane]-2-carboxylic acid, Sodium Salt, 4,4-dioxide The general procedure was followed for the deprotection and salt formation (step 5) using the product of Example 7, Isomer B (30 mg) to give the desired product (12 mg,54% for 2 steps).

IR(D$_2$O): 2956, 1776, 1621, 1389, 1323, 1258, 1116, 840 cm$^{-1}$;

$^1$H NMR(300 MHz, D$_2$O): δ0.11(s,6H), 0.83(s,9H), 1.35 (s,3H), 1.50(s,3H), 1.71–1.75(m,2H), 4.08(s,1H), 4.20(t,1H, J=4.2 Hz), 4.81(s,1H);

$^{13}$C NMR(75 MHz, D$_2$O): δ17.6, 18.0, 18.4, 19.6, 25.3, 37.7, 53.3, 65.9, 66.0, 66.5, 173.3, 180.2;

MS(Electrospray): m/z 388.0 (M+H).

EXAMPLE 10

(2S,5R)-2-[(tert-Butyldimethylsilyl)oxy]-3,3-dimethyl-7-oxospiro[cyclopropane-1,6-[4]thia[1] azabicyclo[3.2.0]-heptane]-2-carboxylic acid, Sodium Salt, 4,4-dioxide The general procedure was followed for the deprotection and salt formation (step 5) using the product of Example 7, Isomer C (50 mg) to give the desired product (12 mg, 32% for 2 steps).

IR(D$_2$O): 2929, 1777, 1628, 1614, 1297, 1113, 829, 780 cm$^{-1}$;

$^1$H NMR(300 MHz, D$_2$O): δ0.10 (s,3H), 0.12 (s,3H), 0.73(s,9H), 1.24(s,3H), 1.38(s,3H), 1.61(m,1H), 1.82(m, 1H), 4.02(s,1H), 4.12(m,1H), 4.91(s,1H);

$^{13}$C NMR(75 MHz, D$_2$O): δ17.6, 18.1, 18.4, 19.7, 25.3, 38.7, 56.2, 65.6, 66.1, 68.4, 173.2, 179.6;

HRMS (C$_{16}$H$_{27}$NO$_6$SSi) Calcd. 390.1407, Found 390.1394 (M+H).

EXAMPLE 11

(1S,2S,5R)-2-cyclohexyloxy-3,3-dimethyl-7-oxospiro[cyclo-propane-1,6-[4]thia[1]azabicyclo[3.2.0]heptane]-2-carboxylic acid, Diphenyl Methyl ester, 4.4-dioxide (Isomer A)

(1R,2S,5R)-2-cyclohexyloxy-3,3-dimethyl-7-oxospiro[cyclo-propane-1,6-[4]thia[1]azabicyclo[3.2.0]-heptane]-2-carboxylic acid, Diphenyl Methyl ester, 4.4-dioxide (Isomer B) and (2S,5R)-2-cyclohexyloxy-3,3-dimethyl-7-oxospiro[cyclo-propane-1,6-[4]thia[1]azabicyclo[3.2.0]heptane]-2-carboxylic acid, Diphenyl Methyl ester, 4.4-dioxide (Isomer C)

The general procedure was followed for the insertion reaction (step 4) using 6-diazo penicillanic acid sulfone diphenylmethyl ester(500 mg, 1.17 mmol) and cyclohexyl vinyl ether(297 mg, 2.35 mmol) to obtain the product (363 mg) as a mixture of 3 isomers(59%). Pure Isomer A (1137 mg), Isomer B (133 mg) and Isomer C (93 mg) were obtained by column chromatography (Silica Gel: hexane gradient to 15% ethyl acetate).

Isomer A

IR(CDCl$_3$): 2934, 1797, 1758, 1324, 1118, 701 cm$^{-1}$;
$^1$H NMR(300 MHz, CDCl$_3$): δ1.14(s,3H), 1.25(m,6H), 1.58(s,3H), 1.73(m,4H), 1.91(m,2H), 3.45(m,1H), 3.92(m,1H), 4.46(s,1H), 4.60(s,1H), 6.98(s,1H), 7.32–7.38(m,10H);
MS(Electrospray): m/z 423.9 (M+H).

Isomer B

IR(CDCl$_3$): 2935, 1795, 1757, 1173, 1117, 704 cm$^{-1}$;
$^1$H NMR(300 MHz, CDCl$_3$): δ1.08(s,3H), 1.23–1.32(m, 7H), 1.57(s,3H), 1.71(m,3H), 1.86(m,2H), 3.67(m,1H), 4.03(m,1H), 4.47(s,1H), 4.70(s,1H), 7.00(s,1H), 7.30–7.40(m, 10H);
MS(Electrospray): m/z 423.9 (M+H).

Isomer C

IR(CDCl$_3$): 2933, 1796, 1758, 1321, 1117, 700 cm$^{-1}$ ;
$^1$H NMR(300 MHz, CDCl$_3$): δ1.12(s,3H), 1.17–1.36(m, 7H), 1.56(s,3H), 1.73(m,3H), 1.88(m,2H), 3.61(m,1H), 3.89(m,1H), 4.50(s,1H), 4.58(s,1H), 6.97(s,1H), 7.31–7.39(m, 10H);
MS(Electrospray): m/z 423.9 (M+H).

EXAMPLE 12

(1S,2S,5R)-2-cyclohexyloxy-3,3-dimethyl-7-oxospiro[cyclo-propane-1,6-[4]thia[1]azabicyclo[3.2.0]heptane]-2-carboxylic acid, Sodium Salt, 4.4-dioxide The general procedure was followed for the deprotection and salt formation (step 5) using the product of Example 12, Isomer A (55 mg) to give the desired product (28 mg, 70% for 2 steps).

IR(D$_2$O): 3423, 2934, 1779, 1625, 1320, 1115 cm$^{-1}$;
$^1$H NMR(300 MHz, D$_2$O): δ1.25(m, 7H), 1.47(s, 3H), 1.60(s, 3H), 1.73(m, 3H), 1.87(m, 2H), 3.75(m, 1H), 4.18(s, 1H), 4.26(m, 1H), 4.56(s, 1H);
MS(Electrospray): m/z 355.9 (M–H).

EXAMPLE 13

(1R,2S,5R)-2-cyclohexyloxy-3,3-dimethyl-7-oxospiro[-cyclo-propane-1,6-[4]thia[1]azabicyclo[3.2.0]heptane]-2-carboxylic acid, Sodium Salt, 4.4-dioxide The general procedure was followed for the deprotection and salt formation (step 5) using the product of Example 12, Isomer B (100 mg) to give the desired product (51 mg, 71% for 2 steps).

IR(D$_2$O): 3369, 2932, 1770, 1632, 1022 cm$^{-1}$;
$^1$H NMR(300 MHz, D$_2$O): δ1.29(m,6H), 1.45(s,3H), 1.59(s,3H), 1.72(m,3H), 1.84(m,1H), 1.92(m,2H), 3.71(m,1H), 4.19(m,2H), 4.82(s,1H);
MS(Electrospray): m/z 355.9 (M–H).

EXAMPLE 14

(2S,5R)-2-cyclohexyloxy-3,3-dimethyl-7-oxospiro[cyclo-propane-1,6-[4]thia[1]azabicyclo[3.2.0]heptane]-2-carboxylic acid, Sodium Salt, 4.4-dioxide The general procedure was followed for the deprotection and salt formation (step 5) using the product of Example 12, Isomer C (60 mg) to give the desired product (34 mg for 2 steps).

IR(D$_2$O): 3433, 2935, 1777, 1618, 1304, 1114 cm$^{-1}$;
$^1$H NMR(300 MHz, D$_2$O): δ1.25(m,6H), 1.44(s,3H), 1.58(s,3H), 1.72(m,2H), 1.84(dd,1H,J=7.92 and 5.37 Hz), 1.92(m,1H), 2.01(t,1H,J=7.6 Hz), 2.03(m,1H), 3.68(m,1H), 4.18(s,1H), 4.25(dd,1H,J=7.11 and 5.34 Hz), 4.62(s,1H);
MS(Electrospray): m/z 355.9 (M–H).

What is claimed is:

1. A compound of Formula (I)

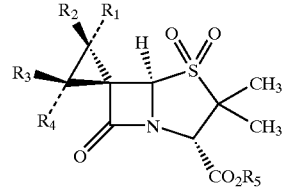

Formula (I)

wherein:

R$_1$, R$_2$, R$_3$, and R$_4$ are independently selected from H, —OH and —OR$_6$;

R$_5$ is selected from hydrogen, an alkali metal cation, an alkaline earth metal cation, ammonium, tetraalkylammonium, alkyl of 1 to 12 carbon atoms, cycloalkyl of 3 to 10 carbon atoms, alkenyl of 2 to 12 carbon atoms, aralkyl of 7 to 20 carbon atoms, aryl of 6 to 12 carbon atoms and moieties of the formulae:

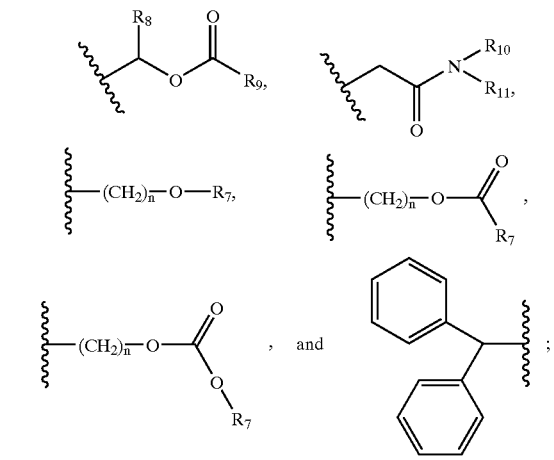

R$_6$ is selected from alkyl of 1 to 12 carbon atoms optionally substituted with alkoxy, halogen, dialkylamino, —Oalkyloalkyl, and 1 or 2 phenyl groups; cycloalkyl of 3 to 10 carbon atoms; alkenyl of 2 to 12 carbons; alkyloxacyclopropyl of 3 to 12 carbon atoms; aryl of 6 to 12 carbon atoms; heteroaryl having 5 or 6 ring atoms; bicyclic heteroaryl having 8 to 20 ring atoms; heteroarylalkyl having 5 or 6 ring atoms; and —SiR$_{12}$R$_{13}$R$_{14}$;

n is an integer of 1 to 3;

R$_7$ is alkyl of 1 to 12 carbon atoms; cycloalkyl of 3 to 10 carbon atoms; aralkyl of 7 to 20 carbon atoms; or aryl of 6 to 12 carbon atoms;

R$_8$, R$_9$, R$_{10}$ and R$_{11}$ are independently selected from alkyl of 1 to 12 carbon atoms;

R$_{12}$, R$_{13}$, and R$_{14}$ are independently selected from alkyl of 1 to 12 carbon atoms optionally substituted with —OCOR$_7$, —CO$_2$R$_7$, alkenyl of 2 to 12 carbon atoms, cycloalkyl of 3 to 10 carbon atoms, and aryl of 6 to 12 carbon atoms; optionally two of R$_{12}$, R$_{13}$, and R$_{14}$ taken together with the silicon atom to which they are attached form a cyclic ring of 5 or 6 ring atoms;

provided that at least one of R$_1$, R$_2$, R$_3$, and R$_4$ is hydrogen; or a pharmaceutically acceptable salt thereof.

2. A compound according to claim 1 wherein:

R$_5$ is selected from H, sodium, potassium and lithium.

3. A compound according to claim 1 wherein:

R$_5$ is selected from aralkyl of 7 to 20 carbon atoms,

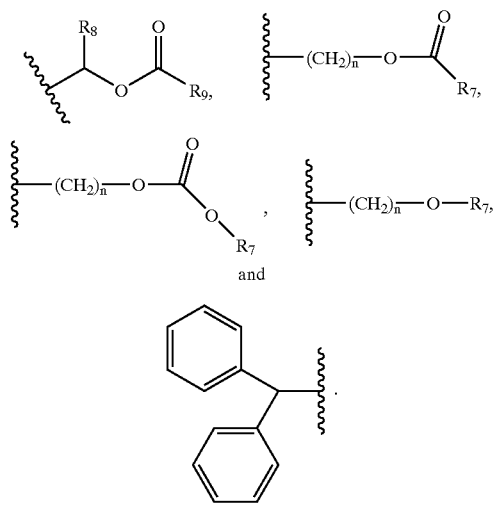

4. A compound according to claim 1 wherein

R$_5$ is selected from H, Na, Li, K,

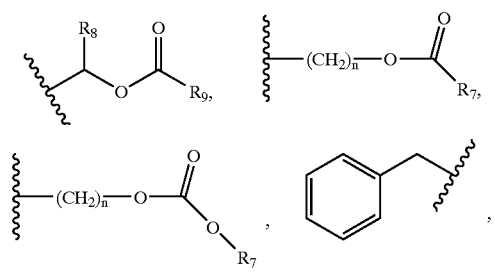

-continued

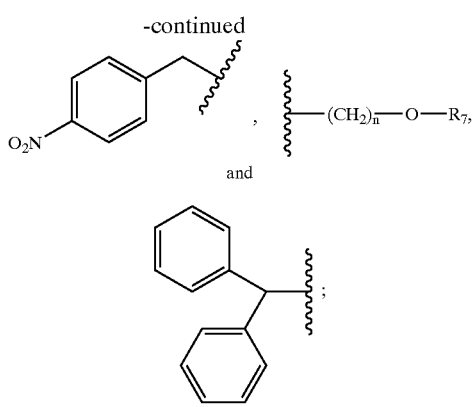

R$_1$ is selected from —OCH$_3$, —OCH$_2$CH$_2$OCH$_3$, —OCH$_2$CH$_2$Cl, —OCH$_2$CH$_2$N(CH$_3$)$_2$, —O-cyclohexyl, —OC(CH$_3$)$_2$CH$_2$CH$_3$, —OCH=CHCH$_3$, —OCH$_2$ (tetrahydrofuran), —OCH$_2$CH$_2$OCH$_2$CH$_2$OCH$_2$CH$_3$, —OSi(CH$_3$)$_2$t-butyl, —OSi(CH$_3$)$_2$phenyl, —OSi(CH$_3$)$_2$CH$_2$CH=CH$_2$, —OSi(CH$_3$)$_2$CH$_2$CH$_3$, —OSi(CH$_3$)$_2$i-propyl, —OSi(CH$_3$)$_2$CHCH$_2$, —OSi(CH$_3$)$_2$CH$_2$CH$_2$OCOCH$_3$, —OSi(phenyl)$_3$, —OCH$_2$CH=CH$_2$, —O-t-butyl, —OCH(phenyl)$_2$, —OSiMe$_2$(cyclohexyl)

and 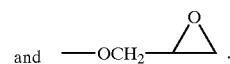

5. A compound according to claim 1 wherein:

R$_6$ is selected from alkyl of 1 to 12 carbon atoms optionally substituted with alkoxy, halogen, dialkylamino, —Oalkyloalkyl, and 1 or 2 phenyl groups; cycloalkyl of 3 to 10 carbon atoms; alkenyl of 2 to 12 carbon atoms; alkyloxacyclopropyl of 3 to 12 carbon atoms; aryl of 6 to 12 carbon atoms; heteroaryl having 5 or 6 ring atoms; bicyclic heteroaryl having 8 to 20 ring atoms; and heteroarylalkyl having 5 or 6 ring atoms.

6. A compound according to claim 1 wherein R$_6$ is —SiR$_{12}$R$_{13}$R$_{14}$.

7. A compound according to claim 1 wherein:

R$_1$ is —OR$_6$;

R$_2$, R$_3$, and R$_4$ are H;

R$_5$ is selected from H, Na, Li, K,

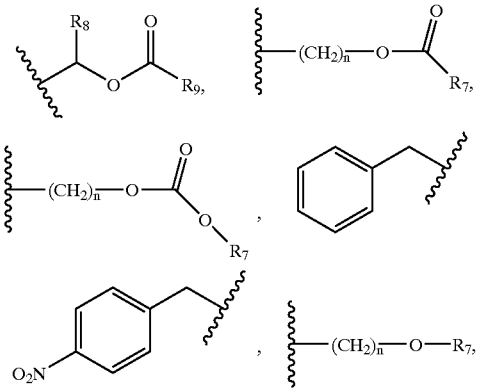

-continued

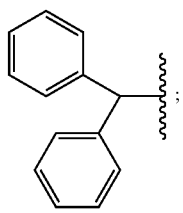

8. A compound according to claim 1 wherein:

$R_2$ is —$OR_6$;

$R_1$, $R_3$, and $R_4$ are H;

$R_5$ is selected from H, Na, Li, K,

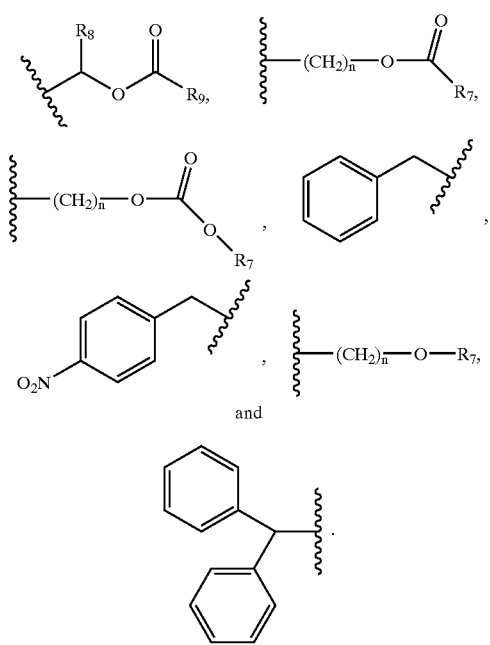

9. A compound according to claim 1 wherein:

$R_3$ is —$OR_6$;

$R_1$, $R_2$, and $R_4$ are H;

$R_5$ is selected from H, Na, Li, K,

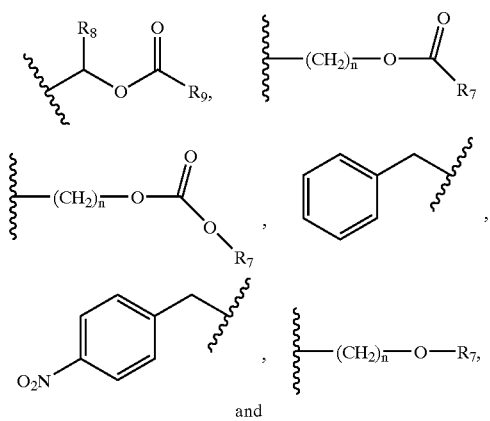

-continued

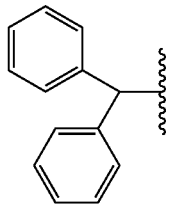

10. A compound according to claim 1 wherein:

$R_4$ is —$OR_6$;

$R_1$, $R_2$, and $R_3$ are H;

$R_5$ is selected from H, Na, Li, K,

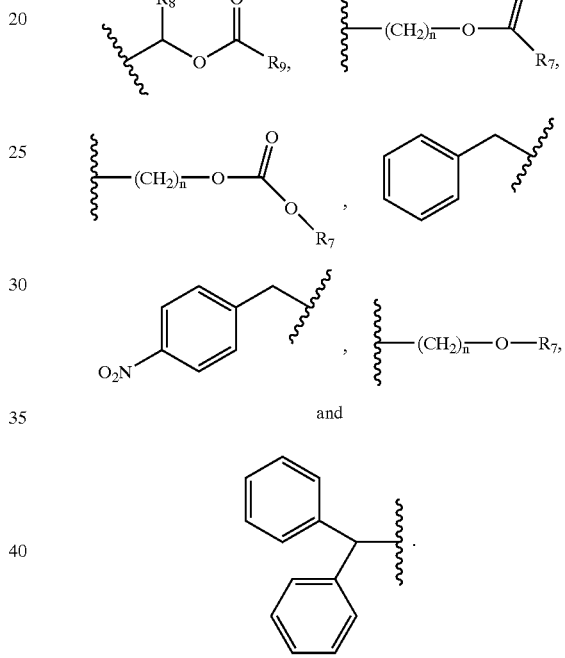

11. A compound according to claim 1 wherein:

$R_5$ is selected from H, Na, Li, K,

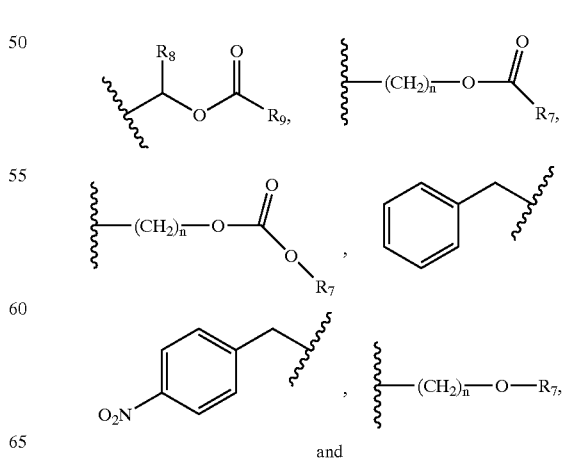

-continued

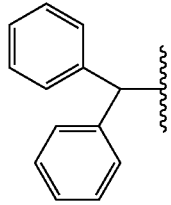

$R_6$ is selected from —$CH_3$, —$CH_2CH_2OCH_3$, —$CH_2CH_2Cl$, —$CH_2CH_2N(CH_3)_2$, -cyclohexyl, and 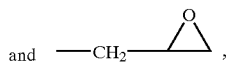, —$C(CH_3)_2CH_2CH_3$, —$CH=CHCH_3$, —$CH_2$ (tetrahydrofuran), —$CH_2CH_2OCH_2CH_2OCH_2CH_3$, —$Si(CH_3)_2$t-butyl, —$Si(CH_3)_2$phenyl, —$Si(CH_3)_2CH_2CH=CH_2$, —$Si(CH_3)_2CH_2CH_3$, —$Si(CH_3)_2$i-propyl, —$Si(CH_3)CH=CH_2$, —$Si(CH_3)_2CH_2CH_2OCOCH_3$, —$Si(phenyl)_3$, —$CH_2CH=CH_2$, -t-butyl, —$CH(phenyl)_2$, —$SiMe_2(cyclohexyl)$, furanyl, pyrazolyl, thienyl, dihydroindolyl, dihydrooxazolyl, dihydropyrimidinyl, benzofuranyl, imidazolyl, pyridyl, tetrazolyl, triazolyl, piperazinyl, indolyl, oxazolyl, piperidinyl, dihydrobenzimidazolyl, tetrahydrofuranyl, benzoxazolyl, isooxazolyl, pyrrolyl, dihydrotriazolyl, and tetrahydrothienyl.

12. A compound according to claim 1 wherein:
$R_5$ is H, Na, Li, K,

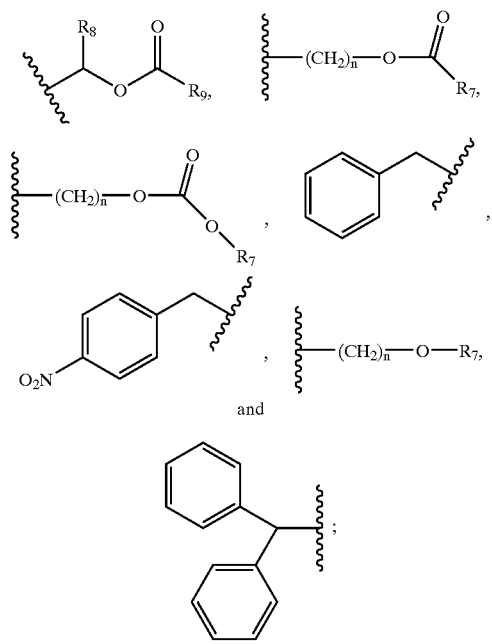

$R_1$, $R_2$, $R_3$ and $R_4$ is independently selected from H, —O-cycloalkyl, —O-alkyl, —O-alkenyl and —$OSiR_{12}R_{13}R_{14}$;
$R_{12}$, $R_{13}$, and $R_{14}$ are independently selected from alkyl; provided that three of $R_1$, $R_2$, $R_3$ and $R_4$ are independently hydrogen.

13. A compound according to claim 1 wherein:
$R_5$ is H, Na, Li, K,

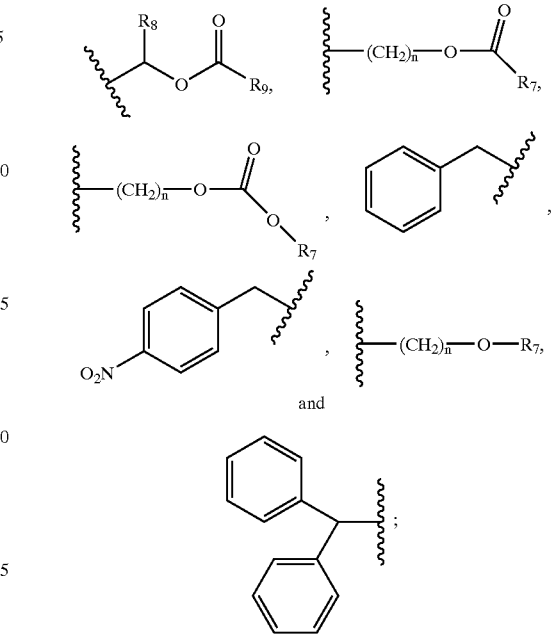

$R_1$, $R_2$, $R_3$ and $R_4$ is independently selected from H, —O-cycloalkyl, —O-alkyl, and —O-alkenyl; provided that three of $R_1R_2$, $R_3$ and $R_4$ are independently hydrogen.

14. A compound according to claim 1 wherein:
$R_5$ is selected from H, Na, Li, and K;
$R_1$, $R_2$, $R_3$ and $R_4$ is independently selected from H, and —$OSiR_{12}R_{13}R_{14}$;
$R_{12}$, $R_{13}$, and $R_{14}$ are independently selected from alkyl; provided that three of $R_1$, $R_2$, $R_3$ and $R_4$ are independently hydrogen.

15. A compound according to claim 1 wherein:
$R_5$ is selected from H, Na, Li,and K;
$R_1$, $R_2$, $R_3$ and $R_4$ is independently selected from H, —O-cycloalkyl, —O-alkyl, and —O-alkenyl; provided that three of $R_1$, $R_2$, $R_3$ and $R_4$ are independently hydrogen.

16. A compound according to claim 1 which is (2S,5R)-2-(Diphenylmethoxy)-3,3-dimethyl-7-oxospiro[cyclopropane-1,6-[4]thia[1]azabicyclo[3.2.0]-heptane]-2-carboxylic acid, diphenylmethyl ester, 4,4-dioxide.

17. A compound according to claim 1 which is (1S,2S,5R)-2-tert-Butoxy-3,3-dimethyl-7-oxospiro[cyclo-propane-1,6-[4]thia[1]azabicyclo[3.2.0]-heptane]-2-carboxylic acid, diphenylmethyl ester, 4,4-dioxide (Isomer A).

18. A compound according to claim 1 which is (1R,2S, 5R)-2-tert-butoxy-3,3-dimethyl-7-oxospiro[cyclo-propane-1,6-[4]thia[1]azabicyclo[3.2.0]heptane]-2-carboxylic acid, diphenylmethyl ester, 4,4-dioxide (Isomer B).

19. A compound according to claim 1 which is (2S,5R)-2-tert-butoxy-3,3-dimethyl-7-oxospiro[cyclopropane-1,6-[4]thia[1]azabicyclo[3.2.0]heptane]-2-carboxylic acid, diphenylmethyl ester, 4,4-dioxide (Isomer C).

20. A compound according to claim 1 which is (1S,2S, 5R)-2-[(tert-Butyldimethylsilyl)oxy]-3,3-dimethyl-7-oxospiro[cyclopropane-1,6-[4]thia[1]azabicyclo[3.2.0]-heptane]-2-carboxylic acid, diphenylmethyl ester, 4,4-dioxide, (Isomer A).

21. A compound according to claim 1 which is (1R,2S,5R)-2-[(tert-Butyldimethylsilyl)oxy]-3,3-dimethyl-7-oxospiro[cyclopropane-1,6-[4]thia[1]azabi-cyclo[3.2.0]-heptane]-2-carboxylic acid, diphenylmethyl ester, 4,4-dioxide (Isomer B).

22. A compound according to claim 1 which is (2S,5R)-2-[(tert-Butyldimethyl silyl)oxy]-3,3-dimethyl-7-oxospiro[cyclopropane-1,6-[4]thia[1]azabicyclo[3.2.0]-heptane]-2-carboxylic acid, diphenylmethyl ester, 4,4-dioxide (Isomer C).

23. A compound according to claim 1 which is (1S,2S,5R)-3,3-Dimethyl-7-oxo-2-(2-propenyl-oxy)spiro[cyclopropane-1,6-[4]thia[1]aza-bi-cyclo[3.2.0]heptane]-2-carboxylic acid, diphenylmethyl ester, 4,4-dioxide, (Isomer A).

24. A compound according to claim 1 which is (1R,2S,5R)-3,3-Dimethyl-7-oxo-2-(2-propenyl-oxy)spiro[cyclopropane-1,6-[4]thia[1]azabi-cyclo[3.2.0]heptane]-2-carboxylic acid, diphenylmethyl ester, 4,4,-dioxide (Isomer B).

25. A compound according to claim 1 which is (1S,2S,5R)-2-[(tert-Butyldimethylsilyl)oxy]-3,3-dimethyl-7-oxospiro[cyclopropane-1,6-[4]thia[1]azabicyclo[3.2.0]-heptane]-2-carboxylic acid, sodium salt, 4,4-dioxide.

26. A compound according to claim 1 which is (1R,2S,5R)-2-[(tert-Butyldimethylsilyl)oxy]-3,3-dimethyl-7-oxospiro[cyclopropane-1,6-[4]thia[1]azabicyclo[3.2.0]-heptane]-2-carboxylic acid, sodium salt, 4,4-dioxide.

27. A compound according to claim 1 which is (2S,5R)-2-[(tert-Butyldimethylsilyl)oxy]-3,3-dimethyl-7-oxospiro[cyclopropane-1,6-[4]thia[1]azabicyclo[3.2.0]-heptane]-2-carboxylic acid, sodium salt, 4,4-dioxide.

28. A compound according to claim 1 which is (1S,2S,5R)-2-cyclohexyloxy-3,3-dimethyl-7-oxospiro[cyclopropane-1,6-[4]thia[1]azabicyclo[3.2.0]heptane]-2-carboxylic acid,diphenyl methyl ester, 4.4-dioxide (Isomer A).

29. A compound according to claim 1 which is (1R,2S,5R)-2-cyclohexyloxy-3,3-dimethyl-7-oxospiro[cyclopropane-1,6-[4]thia[1]azabicyclo[3.2.0]-heptane]-2-carboxylic acid,diphenyl methyl ester, 4.4-dioxide (Isomer B).

30. A compound according to claim 1 which is (2S,5R)-2-cyclohexyloxy-3,3-dimethyl-7-oxospiro[cyclo-propane-1,6-[4]thia[1]azabicyclo[3.2.0]heptane]-2-carboxylic acid, diphenyl methyl ester, 4.4-dioxide (Isomer C).

31. A compound according to claim 1 which is (1S,2S,5R)-2-cyclohexyloxy-3,3-dimethyl-7-oxospiro[cyclopropane-1,6-[4]thia[1]azabicyclo[3.2.0]heptane]-2-carboxylic acid, sodium salt, 4.4-dioxide.

32. A compound according to claim 1 which is (1R,2S,5R)-2-cyclohexyloxy-3,3-dimethyl-7-oxospiro[cyclopropane-1,6-[4]thia[1]azabicyclo[3.2.0]heptane]-2-carboxylic acid, sodium salt, 4.4-dioxide.

33. A compound according to claim 1 which is (1R,2S,5R)-2-cyclohexyloxy-3,3-dimethyl-7-oxospiro[cyclopropane-1,6-[4]thia[1]azabicyclo[3.2.0]heptane]-2-carboxylic acid, sodium salt, 4.4-dioxide.

34. A compound according to claim 1 which is (2S,5R)-2-cyclohexyloxy-3,3-dimethyl-7-oxospiro[cyclo-propane-1,6-[4]thia[1]azabicyclo[3.2.0]heptane]-2-carboxylic acid, sodium salt, 4.4-dioxide.

35. A compound of the Formula (II)

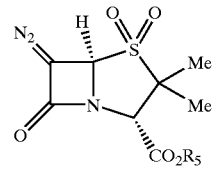

wherein:

$R_5$ is selected from hydrogen, an alkali metal cation, an alkaline earth metal cation, ammonium, tetraalkylammonium, alkyl of 1 to 12 carbon atoms, cycloalkyl of 3 to 10 carbon atoms, alkenyl of 2 to 12 carbon atoms, aralkyl of 7 to 20 carbon atoms, aryl of 6 to 12 carbon atoms and moieties of the formulae:

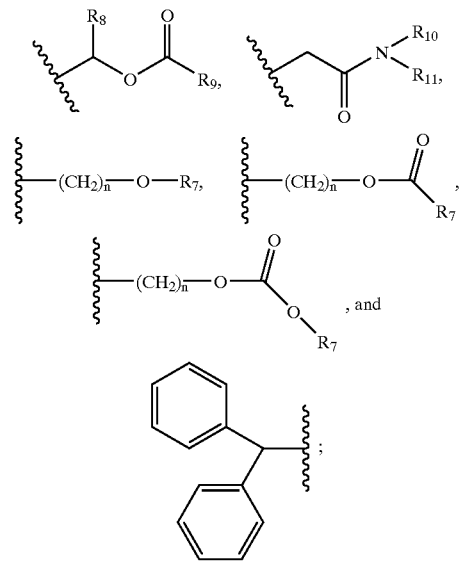

n is an integer of 1 to 3;

$R_7$ is alkyl of 1 to 12 carbon atoms; cycloalkyl of 3 to 10 carbon atoms; aralkyl of 7 to 20 carbon atoms; or aryl of 6 to 12 carbon atoms;

$R_8$, $R_9$, $R_{10}$ and $R_{11}$ are independently selected from alkyl of 1 to 12 carbon atoms;

or a pharmaceutically acceptable salt thereof.

36. A pharmaceutical composition of matter comprising an betalactamase inhibiting effective amount of a compound according to claim 1 and one or more pharmaceutically acceptable carriers.

37. A method of treating bacterial infections in mammals which comprises administering an effective betalactamase inhibiting amount of a compound according to claim 1 in combination with a beta-lactam antibiotic.

38. A process for the preparation of a compound of Formula (I):

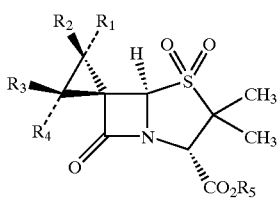

Formula (I)

wherein:

$R_1$, $R_2$, $R_3$, and $R_4$ are independently selected from H, —OH and —$OR_6$;

$R_5$ is selected from hydrogen, an alkali metal cation, an alkaline earth metal cation, ammonium, tetraalkylammonium, alkyl of 1 to 12 carbon atoms, cycloalkyl of 3 to 10 carbon atoms, alkenyl of 2 to 12 carbon atoms, aralkyl of 7 to 20 carbon atoms, aryl of 6 to 12 carbon atoms and moieties of the formulae:

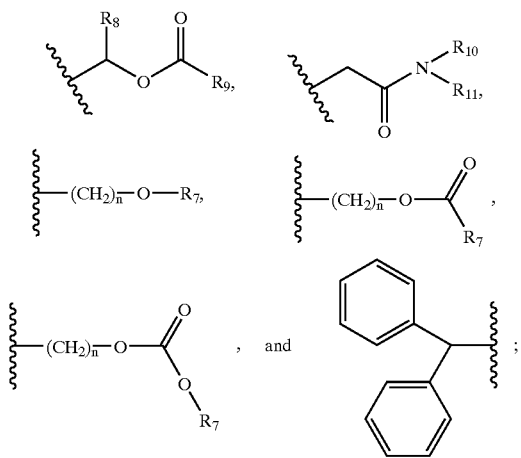

$R_6$ is selected from alkyl of 1 to 12 carbon atoms optionally substituted with alkoxy, halogen, dialkylamino, —Oalkyloalkyl, and 1 or 2 phenyl groups; cycloalkyl of 3 to 10 carbon atoms; alkenyl of 2 to 12 carbon atoms; alkyloxacyclopropyl of 3 to 12 carbon atoms; aryl of 6 to 12 carbon atoms; heteroaryl having 5 or 6 ring atoms; bicyclic heteroaryl having 8 to 20 ring atoms; heteroarylalkyl having 5 or 6 ring atoms; and —$SiR_{12}R_{13}R_{14}$;

n is an integer of 1 to 3;

$R_7$ is selected from alkyl of 1 to 12 carbon atoms; cycloalkyl of 3 to 10 carbon atoms; aralkyl of 7 to 20 carbon atoms; and aryl of 6 to 12 carbon atoms;

$R_8$, $R_9$, $R_{10}$ and $R_{11}$ are independently selected from alkyl of 1 to 12 carbon atoms;

$R_{12}$, $R_{13}$, and $R_{14}$ are independently selected from alkyl of 1 to 12 carbon atoms optionally substituted with —$OCOR_7$, —$CO_2R_7$, alkenyl of 2 to 12 carbon atoms, cycloalkyl of 3 to 10 carbon atoms, and aryl of 6 to 12 carbon atoms; optionally two of $R_{12}$, $R_{13}$, and $R_{14}$ taken together with the silicon atom to which they are attached form a cyclic ring of 5 or 6 ring atoms;

provided that at least one of $R_1$, $R_2$, $R_3$, and $R_4$ is hydrogen;

or a pharmaceutically acceptable salt thereof comprising the steps of:

a) oxidizing 6-aminopenicillanic acid under suitable oxidizing conditions to afford 6-aminopenicillanic acid 4,4-dioxide; and b) treating the compound in step a under suitable ester forming conditions to form a 6-aminopenicillanate 4,4-dioxide hydrochloride;

c) treating the compound in step b as the free amine with sodium nitrite and perchloric acid in an organic solvent-water biphasic mixture to form 6-diazopencillanate 4,4-dioxide;

d) treating the compound in step c by an insertion reaction in the presence of an olefin $R_1R_2$=$R_3R_4$ and a suitable catalyst to form a 7-oxospiro(cyclopropane) penicillanate 4,4-dioxide; and e) deprotecting the compound of step d and optionally forming a salt under suitable conditions.

* * * * *

UNITED STATES PATENT AND TRADEMARK OFFICE
CERTIFICATE OF CORRECTION

PATENT NO. : 6,489,316 B2
DATED : January 20, 2003
INVENTOR(S) : Vincent P. Sandanayaka and Amarnauth S. Prashad It is certified that error appears in the above-identified patent and that said Letters Patent is hereby corrected as shown below:

Column 2,
Line 61, should read -- -OalkylOalkyl --

Column 4,
Line 28, should read -- -OSi(CH$_3$)$_2$$i$-propyl --
Line 41, should read -- -OalkylOalkyl --

Column 7,
Line 63, "-O-alkenyl and", is repeated and should be omitted

Column 8,
Line 55, should read -- thia[1] --

Column 16,
Line 51, should read -- 1N --
Line 52, should read -- was --

Column 18,
Line 59, should read -- 1N --

Column 20,
Lines 37 and 41, should read -- (tert-Butyldimethylsilyl) --

Column 25,
Line 1, should read -- -OalkylOalkyl --

Column 26,
Line 37, should read -- -OalkylOalkyl --

UNITED STATES PATENT AND TRADEMARK OFFICE
CERTIFICATE OF CORRECTION

PATENT NO. : 6,489,316 B2
DATED : January 20, 2003
INVENTOR(S) : Vincent P. Sandanayaka and Amarnauth S. Prashad It is certified that error appears in the above-identified patent and that said Letters Patent is hereby corrected as shown below:

<u>Column 31,</u>
Line 7, should read -- (tert-Butyldimethylsilyl) --

<u>Column 33,</u>
Line 42, should read -- -OalkylOalkyl --

Signed and Sealed this

Seventeenth Day of June, 2003

JAMES E. ROGAN
*Director of the United States Patent and Trademark Office*